US012702710B2

(12) United States Patent
Merchant

(10) Patent No.: US 12,702,710 B2
(45) Date of Patent: Aug. 11, 2026

(54) COMBINATION THERAPY OF MDNA55 AND A VASCULAR ENDOTHELIAL GROWTH FACTOR A (VEGF-A)

(71) Applicant: Medicenna Therapeutics Inc., Toronto (CA)

(72) Inventor: Fahar Merchant, Vancouver (CA)

(73) Assignee: Medicenna Therapeutics Inc., Toronto (CA)

( * ) Notice: Subject to any disclaimer, the term of this patent is extended or adjusted under 35 U.S.C. 154(b) by 439 days.

(21) Appl. No.: 18/248,601

(22) PCT Filed: Oct. 12, 2021

(86) PCT No.: PCT/CA2021/051433

§ 371 (c)(1),
(2) Date: Apr. 11, 2023

(87) PCT Pub. No.: WO2022/077102

PCT Pub. Date: Apr. 21, 2022

(65) Prior Publication Data

US 2023/0405115 A1 Dec. 21, 2023

Related U.S. Application Data

(60) Provisional application No. 63/090,663, filed on Oct. 12, 2020.

(51) Int. Cl.

| | |
|---|---|
| ***A61K 38/20*** | (2006.01) |
| ***A61K 38/45*** | (2006.01) |
| ***A61K 39/395*** | (2006.01) |
| ***A61K 47/42*** | (2017.01) |
| ***A61K 47/46*** | (2006.01) |
| ***A61K 49/10*** | (2006.01) |
| ***A61K 49/14*** | (2006.01) |
| ***A61P 35/00*** | (2006.01) |
| ***C07K 14/54*** | (2006.01) |
| ***C07K 16/22*** | (2006.01) |
| *A61K 39/00* | (2006.01) |

(52) U.S. Cl.

CPC ...... *A61K 39/3955* (2013.01); *A61K 38/2026* (2013.01); *A61K 38/45* (2013.01); *A61K 47/42* (2013.01); *A61K 47/46* (2013.01); *A61K 49/105* (2013.01); *A61K 49/143* (2013.01); *A61P 35/00* (2018.01); *C07K 14/5406* (2013.01); *C07K 16/22* (2013.01); *A61K 2039/505* (2013.01); *A61K 2039/54* (2013.01); *A61K 2039/545* (2013.01)

(58) Field of Classification Search

CPC ............ A61K 38/2026; A61K 39/3955; C07K 14/5406; C07K 16/22

See application file for complete search history.

(56) References Cited

U.S. PATENT DOCUMENTS

| | | | |
|---|---|---|---|
| 6,011,002 A | 1/2000 | Pastan et al. | |
| 6,028,176 A | 2/2000 | Greve et al. | |
| 6,130,318 A | 10/2000 | Wild et al. | |
| 6,335,426 B1 | 1/2002 | Shanafelt et al. | |
| 6,673,602 B1 | 1/2004 | Spear et al. | |
| 6,737,511 B1 | 5/2004 | Youle et al. | |
| 9,512,194 B2 | 12/2016 | Garcia et al. | |
| 9,629,899 B2 | 4/2017 | Puri | |
| 10,093,708 B2 | 10/2018 | Merchant | |
| 10,106,592 B2 | 10/2018 | Merchant | |
| 2003/0013851 A1 | 1/2003 | Powers et al. | |
| 2004/0248260 A1 | 12/2004 | Heavner et al. | |
| 2005/0106148 A1 | 5/2005 | Kay et al. | |
| 2006/0035856 A1 | 2/2006 | Caput et al. | |
| 2007/0160658 A1 | 7/2007 | Connor et al. | |
| 2008/0160029 A1* | 7/2008 | Fyfe | A61K 31/555 424/145.1 |
| 2010/0183545 A1* | 7/2010 | Puri | A61K 38/2026 424/85.2 |
| 2010/0317577 A1 | 12/2010 | Youle | |
| 2011/0023680 A1 | 2/2011 | Wang | |
| 2011/0319336 A1 | 12/2011 | Kawakami et al. | |
| 2012/0294931 A1 | 11/2012 | Kim et al. | |
| 2014/0050709 A1 | 2/2014 | Leen et al. | |
| 2016/0151490 A1 | 6/2016 | Sampath et al. | |
| 2016/0271231 A1 | 9/2016 | Merchant | |
| 2016/0340649 A1 | 11/2016 | Brown et al. | |
| 2019/0016797 A1 | 1/2019 | Arenas-Ramirez et al. | |

FOREIGN PATENT DOCUMENTS

| | | |
|---|---|---|
| CN | 102792358 | 3/2015 |
| EP | 3428647 A1 | 1/2019 |
| JP | 6936934 B2 | 9/2021 |
| WO | WO1994004680 A1 | 3/1994 |
| WO | WO2001018051 A2 | 9/2000 |
| WO | WO2001025282 A1 | 4/2001 |

(Continued)

OTHER PUBLICATIONS

Clinical trial NCT02858895, version 1, Aug. 3, 2016.*

Hallett, Miranda A et al. "Cytokine stimulation of epithelial cancer cells: the similar and divergent functions of IL-4 and IL-13." Cancer research vol. 72,24 (2012): 6338-43. doi: 10.1158/0008-5472.CAN-12-3544.

Kawakami, Mariko et al. "Interleukin-4-Pseudomonas exotoxin chimeric fusion protein for malignant glioma therapy." Journal of neuro-oncology vol. 65,1 (2003): 15-25. doi:10.1023/a:1026294416718.

Agholme et al. "An in vitro model for neuroscience: differentiation of SH-SYSY cells into cells with morphological and biochemical characteristics of mature neurons." J Alzheimer's Disease 20: 1069-1082, 2010.

(Continued)

*Primary Examiner* — Xiaozhen Xie

(74) *Attorney, Agent, or Firm* — Sara Sims; Christina A. MacDougall; Morgan, Lewis & Bockius, LLP

(57) ABSTRACT

Methods for treating a central nervous system (CNS) tumor in a subject, comprising administering to the subject MDNA55 in combination with a vascular endothelial growth factor A (VEGF-A) inhibitor administered at a subtherapeutic level.

17 Claims, 3 Drawing Sheets

Specification includes a Sequence Listing.

(56) References Cited

FOREIGN PATENT DOCUMENTS

| | | | |
|---|---|---|---|
| WO | WO2001034645 | A2 | 5/2001 |
| WO | WO2001062933 | A3 | 8/2001 |
| WO | WO2002018422 | A1 | 3/2002 |
| WO | WO2006074451 | A2 | 7/2006 |
| WO | WO2007146046 | A2 | 12/2007 |
| WO | WO2008101671 | A2 | 8/2008 |
| WO | WO2009029601 | A2 | 3/2009 |
| WO | WO2009140598 | A1 | 5/2009 |
| WO | WO2010031185 | A1 | 3/2010 |
| WO | WO2011106779 | A1 | 9/2011 |
| WO | WO2012054929 | A2 | 4/2012 |
| WO | WO2012088446 | A1 | 6/2012 |
| WO | WO2012139112 | A1 | 10/2012 |
| WO | WO2013112871 | A1 | 8/2013 |
| WO | WO2015042705 | A1 | 9/2014 |
| WO | WO2015042707 | A1 | 4/2015 |
| WO | WO2015070210 | A1 | 5/2015 |
| WO | WO2015117229 | A1 | 8/2015 |
| WO | WO2016040441 | A1 | 3/2016 |
| WO | WO2018112266 | A1 | 6/2018 |
| WO | WO2019051204 | A1 | 3/2019 |
| WO | WO2019073299 | A1 | 4/2019 |
| WO | WO2020160639 | A1 | 8/2020 |
| WO | WO2021258213 | A1 | 12/2021 |

OTHER PUBLICATIONS

Allen et al. "Interleukin-13 Displaying Retargeted Oncolytic Measles Virus Strains Have Significant Activity Against Gliomas With Improved Specificity". Molecular Therapy, Sep. 2008 (Sep. 2008), vol. 16, No. 9, pp. 1556-1564, ISSN 1525-0016 See whole document.

"Alzheimer's Disease", ninds.nih.gov/disorders/alzheimersdisease/alzheimersdisease.htm; Jan. 4, 2012; 3 total pages.

Bachran et al. "Anthrax Toxin-Mediated Delivery of the Pseudomonas Exotoxin A Enzymatic Domain to the Cytosol of Tumor Cells via Cleavable Ubiquitin Fusions" mBio vol. 4, 00. 201-213 (2013).

Bates, D.L., et al., "3QB7: Interleukin-4 mutant RGA bound to cytokine receptor common qamma," «RCSB PDB> Protein Data Bank, oaqes 1-2 (Apr. 25, 2012).

Baeurle Patrick A. et al. "Bispecific T-cell engaging antibodies for cancer therapy", Cancer Research, AACR, US Philadephia, PA, vol. 69, No. 12, Jun. 15, 2009 (Jun. 15, 2009), pp. 4941-4944, XP002665118, ISSN: 1538-7445, CAN-09-0547 [retrieved on Jun. 9, 2009] the whole document.

Bhatia et al., Innovative approaches for enhancing cancer gene therapy. Discovery Medicine 15(84): 309-317, 2013.

Boise et al. "bcl-x, a bcl-2-Related Gene That Functions as a Dominant Regulator of Apoptotic Cell Death" Cell, vol. 74, oo.597-608 (1993).

Burt, B.M. et al. "Expression of Interleukin-4 Receptor Alpha in Human Pleural Mesothelioma Is Associated with Poor Survival and Promotion of Tumor Inflammation". Clinical Cancer Research, Mar. 15, 2012 (Mar. 15, 2012), vol. 18, No. 6, pp. 1568-1577 See entire document.

Cao et al., In vivo delivery of a Bel-xi fusion protein containing the TAT protein transduction domain protects against ischemic brain injury and neuronal apoptosis. J Neurosci 22(13):5423-5431, 2002.

Candolfini et al. "Gene therapy-mediated delivery of targeted cytotoxin for glioma therapeutics". Proceedings of the National Academy of Sciences of the United States of America, Nov. 16, 2010 (Nov. 16, 2010), vol. 107, No. 46, pp. 20021-20026, ISSN 1091-6490.

Castro et al. "Therapy and Targeted Toxins for Glioma". Current Gene Therapy, Jun. 1, 2011 (Jun. 1, 2011), vol. 11, No. 3, pp. 155-180, ISSN 1875-5631.

C.E. Brown et al.: "Bioactivity and Safety of IL13R?2-Redirected Chimeric Antigen Receptor CD8+ T Cells in Patients with Recurrent Glioblastoma", Clinical Cancer Research, vol. 21, No. 18, Jun. 9, 2015 (Jun. 9, 2015), pp. 4062-4072, XP055362974, US ISSN: 1078-0432, DOI: 10.1158/1072-0432.CCR-15-0428 The whole document.

Cleary et al "Cloning and structural analysis of cDNAs for bcl-2 and a hybrid bcl-2/immunoglobulin transcript resulting from the t(14;18) translocation" Cell Press, vol. 47, No. 1, DD. 19-28 (1986).

Corren et al. "Lebrikizumab treatment in adults with asthma.", N Eng I J Med., Sep. 22, 2011, pp. 1088-1098, 365(1), Massachusetts Medical Society, Waltham, MA.

Creusot, et al., "Engineering cell-type selective immune responses using mechanism- based designer IL-4 cytokines," The Journal of Immunoloov, 186:57.8 (2011).

Cuny, G.D. Neurodegenerative diseases: challenges and opportunities. Future Med Chem 4(13): 1647-1649, 2012.

Diehn et al. "Cancer Stem Cells and Radiotherapy: New Insights Into Tumor Radioresistance" Journal of National Cancer Institute, vol. 98, pp. 1755-1757 (2006).

Eisenmesser et al., "Solution structure of interleukin-13 and insights into receptor engagement." J Mol. Biol., Jun. 2001, pp. 231-241, 310(1), Elsevier, Amsterdam, Netherlands.

Elgert, K. Immunology, understanding the immune system. New York: Wiley-Liss, Inc., 1996; pp. 323-326.

Feigin et al. Recent advances in Huntington's disease: implications for experimental therapeutics. Curr Opin Neural 15: 483-489, 2002.

Fernandez et al. "Genetically Engineered Vesicular Stomatitis Virus in Gene Therapy; Application for Treatment of Malignant Disease". Journal of Virology, Jan. 2002 (2002), vol. 76, No. 2, DD. 895-904, ISSN 0022-538X See whole document.

Fernando, R. et al. "Breast cancer cell proliferation is inhibited by bAD: regulation of cyclin D1." The Journal of biological chemistry vol. 282,39 (2007): 28864-73.

Forster et al. Characterization of differentiated SH-SY5Y as neuronal screening model reveals increased oxidative vulnerability. J Biomlecul Screen 21(5): 496-509, 2016.

Fueller, J. et al. "C-RAF activation promotes BAD polyubiquitylation and turn-over by the proteasome." Biochemical and biophysical research communications vol. 370,4 (2008): 552-6.

Garland, L. et al. "Phase I trial of intravenous IL-4 Pseudomonas Exotoxin protein (NBI-3001) in patients with advanced solid tumors that express the IL-4 receptor". Journal of Immunotherapy, 2005, vol. 28; No. 4, pp. 376-381.

GenBank Accession No. Z23115, bcl XL gene [*Homo sapiens*] Oct. 7, 2008.

GenBank Accession No. 3QB7_A, chain A, Interleukin 4 [*Homo sapiens*] Apr. 25, 2012.

GenBank Accession No. Q07817, bcl gene apotosis [*Homo sapiens*] Feb. 28, 2018.

Halliday et al. Alzheimer's disease and inflammation: a review of cellular and therapeutic mechanisms. Clin Exp Pharmacol Physiol 27: 1-8, 2000.

Han, J. et al. "Analysis of the cancer genome atlas (TCGA) database identifies an inverse relationship between interleukin-13 receptor a1 and a2 gene expression and poor prognosis and drug resistance in subjects with glioblastoma multiforme". Journal of Neuro-Oncology, Nov. 22, 2017 (Nov. 22, 2017), vol. 136, No. 3, pp. 463-474 See entire document.

Harvey, A. "Overview of Cell Signaling Pathways in Cancer." Predictive Biomarkers in Oncology, edited by Sunil Badve and Georqe Louis Kumar. 2019, pp. 167-182.

Hotchkiss et al., TAT-BH4 and TAT-Bel-xi peptides protect against sepsis-induced lymphocyte apoptosis in vivo. J Immunol 176: 5471-5477, 2006.

Ichinose, M. et al. "Extracellular Bad fused to toxin transport domains induces apoptosis." Cancer research vol. 62,5 (2002): 1433-8.

Ito, et al., "Distinct structural requirements for interleukin-4 (IL-4) and IL-13 binding to the shared IL-13 receptor facilitate cellular tuning of cytokine responsiveness." J. Biol. Chem., Sep. 4, 2009, pp. 24289-24296, 284(36), ASBMB, Rockville, MD.

Joshi et al. "In Situ Expression of Interleukin-4 (IL-4) Receptors in Human Brain Tumors and Cytotoxicity of a Recombinant IL-4 Cytotoxin in Primary Glioblastoma Cell Cultures", Cancer Research, Nov. 15, 2001, DD. 8058-8061, vol. 61.

(56) References Cited

OTHER PUBLICATIONS

Juengst, E.T. What next for human gene therapy? BMJ 326: 1410-1411, 2003.
Junttila et al "Redirecting cell-type specific cytokine responses with engineered interleukin-4 superkines" Nat Chem Biol., vol. 8, No. 12, pp. 990-998 (2012).
Kahlon, et al., "Specific Recognition and Killing of Glioblastoma Multiforme by Interleukin 13-Zetakine Redirected Cytolytic T Cells", Cancer Research, 64:9160-9166 (2004).
Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).
Laske et al. "Tumor regression with regional distribution of the targeted toxin TF-CRM107 in patients with malignant brain tumors" Nature, vol. 3, pp. 1362-1368 (1997).
Levin, et al., "Exploiting a natural conformational switch to engineer an interleukin-2 "superkine"," Nature 484:529-533 (A & B) (2012).
Lomonosova and Chinnadurai "BH3-only proteins in apoptosis and beyond: an overview" Oncogene, vol. 27, pp. S2-S19 (2009).
Madhankumar et al., "interleukin 13 mutants of enhanced avidity toward the glioma-associated receptor, IL 13Ralpha2." Neoplasia, Jan./Feb. 2004, pp. 15-22, 6(1), Neoplasia Press, Ann Arbor, MI.
Mardor, Y. et al. "Convection-Enhanced Drug Delivery of Interleukin-4 Pseudomonas Exotoxin (PRX321): Increased Distribution and Magnetic Resonance Marketing". J Pharmacol Exp Ther., Aug. 2009 (Aug. 2009). vol. 330(2), pp. 520-525, ISSN 0022-3565 (Print), 1521-0103 (Electronic), 0022-3565 (Linking) [online] [retrieved on Feb. 12, 2019 (Feb. 12, 2019)].
Mccormick et al. Commentary: IL-4 and IL-13 receptors and signaling. Cytokine 75: 38-50, 2015.
Munitz et al. 2008. PNAS 105:7240-7245 (Year: 2008).
Murray, E.J. "Cloning Genes in Mammalian Cell-lines" in Molecular Biology and Biotechnology. Great Britain: The Royal Society of Chemistry, 2000, pp. 177-201.
Natoli, A et al. "Targeting the IL-4/IL-13 signaling pathway sensitizes Hodgkin lymphoma cells to chemotherapeutic drugs." International journal of cancer vol. 133,8 (2013): 1945-54.
Oshima et al., "Conversion of interleukin-13 into a high affinity agonist by a single amino acid substitution." J. Biol. Chem., May 12, 2000, p. 14375-14380, 275(19), ASBMB, Rockville, MD.
Oshima et al., "Characterization of a powerful high affinity antagonist that inhibits biological activities of human interleukin-13." J. Biol. Chem., May 4, 2001, p. 15185-15191, 276(18), ASBMB, Rockville, MD.
Pahlman et al. Differentiation and survival influences of growth factors in human neuroblastoma. Eur J Cancer 31A(4): 453-458, 1995.
Partaledis et al., "In vitro selection and characterization of human immunodeficiency virus type 1 (HIV-1) isolates with reduced sensitivity to hydroxyethylamino sulfonamide inhibitors of HIV-1 aspartyl protease." J. Viral, Sep. 1995, pp. 5228-5235, 69(9), American Society for Microbiology, Washington DC.
Phillips, A.J. The challenge of gene therapy and DNA delivery. J Pharmacy and Pharmacol53: 1169- 1174,2001.
Polzein, L et al. "Identification of novel in vivo phosphorylation sites of the human proapoptotic protein BAD: pore-forming activity of BAD is regulated by phosphorylation." The Journal of biological chemistry vol. 284,41 (2009): 28004-20.
Post et al. "Targeted Cancer Gene Therapy Using a Hypoxia Inducible Factor- Dependent Oncolytic Andenovirus Armed with Interleukin-4". Cancer Research, Jul. 15, 2007 (Jul. 15, 2007), vol. 67, No. 14, pp. 6872-6881, ISSN 1538-7445 See whole document.
Puri et al. "Human Neurological Cancer Cells Express Interleukin-4 (IL-4) Receptors Which Are Targets For the Toxic Effects Of IL4-Pseudomonas Exotoxin Chimeric Protein". The International Journal of Cancer, 1994, vol. 58, pp. 574-581, ISSN 1097- 0215.
Reynolds et al., "Genetic Instability Induced by the Tumor Microenvironment", Cancer Research, vol. 56, pp. 5754-5757 (1996).
Rochman et al., 2009. 9(7) p. 1-23 (Year: 2009).
Rubanyi, G.M., The future of human gene therapy. Molecular Aspects Med 22: 113-142, 2001.
Rubin "Neuronal cell death: when, why and how" British Medical Bulletin, vol. 53, Issue 3, pp. 617-631 (1997).
Sakariassen et al. "Cancer Stem Cells as Mediators of Treatment Resistance in Brain Tumors: Status and Controversies" Neoplasia, vol. 9, No. 11, pp. 882-892 (2007).
Schnare et al., "Specific Antagonism of Type I IL-4 Receptor with a Mutated Form of Murine IL-4," The Journal of Immunology, 161:7, pp. 3484-3492 (1998).
Sharma et al. "Interleukin-4 Mediates Down Regulation of Antiviral Cytokine Expression and Cytotoxic T-Lymphocyte Responses and Exacerbates Vaccinia Virus Infection In Vivo". Journal of Virology, Oct. 1996, vol. 70, No. 10, pp. 7103-7107, ISSN 0022-538X See whole document.
Shimamura et al. "The IL-4 and IL-13 pseudomonas exotoxins: new hope for brain tumor therapy". Neurosurgical FOCUS, 2006, vol. 20, No. 3:E11, ISSN 1092-0684.
Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).
Steece-Collier et al. Etiology of Parkinson's disease: genetics and environment revisited. Proc Natl Acad Sci USA 99(22): 13972-13974, 2002.
Charo et al. Bcl-2 Overexpression Enhances Tumor-Specific T-Cell Survival. Cancer Res 65(5): 2001-2008, 2005.
Vella et al. Interleukin 4 (IL-4) or IL-7 Prevents the Death of Resting T Cells: Stat6 Is Probably Not Required for the Effect of IL-4. J Exp Med 186(2): 325-330, 1997.
Wilkie et al. Selective Expansion of Chimeric Antigen Receptor-targeted T-cells with Potent Effector Function using Interleukin-4. J Biol Chem 285(33): 25538-25544, 2010 (and supplementary materials) (17 total pages).
Suga et al. "Transplant Immunosuppression Enhances Efficiency of Adenoviral-Mediated Gene Retransfection: Inhibition of Interferon-y and Immunoglobin G" The Society of Thoracic Surgeons, vol. 73, pp. 1092-1097 (2002).
Thompson, et al., "Mutants of interleukin 13 with altered reactivity toward interleukin 13 receptors." J. Biol. Chem., Oct. 15, 1999, pp. 29944-29950, 274(42), ASBMB, Rockville, MD.
Thorpe et al. "Toxicity of diphtheria toxin for lymphoblastoid cells is increased by conjuqation to antilymphocytic qlobulin" Nature, vol. 271, oo. 752-755 (1978).
Tsujimoto and Croce "Analysis of the structure, transcripts, and protein products of bcl-2, the gene involved in human follicular lymphoma" Proc. Natl. Acad. Sci., vol. 83, pp. 5214-5218 (1986).
UniProtKB database P05112 (Aug. 13, 1987).
Vallera, D.A. et al. "Retroviral immunotoxin gene therapy of leukemia in mice using leukemia-specific T cells transduced with an interleukin-3/Bax fusion protein gene." Human gene theraov vol. 14, 18 (2003): 1787-98.
Van Den Broek, et al. "IL-4 and IL-10 Antagonize IL-12-Mediated Protection Against Acute Vaccinia Virus Infection with a Limited Role of IFN-y and Nitric Oxide Synthetase 2". Journal of Immunology, Jan. 1, 2000 (Jan. 1, 2000), vol. 164, No. 1, pp. 371-378, ISSN 1550-6606.
White "Life, Death, and the Pursuit of Apoptosis" Genes and Development 10, pp. 1-15 (1996).
Yang et al. "Bad, a heterodimeric partner for Bel-XL and Bcl-2, displaces Bax and promotes cell death" Cell, vol. 80, pp. 285-291 (1995).
Yang et al. Targeting cancer stern cell pathways for cancer therapy. Signal Transd Targeted Ther 5:8, 2020 (35 total pages).
Yeung et al. Signaling pathways in inflammation and anti-inflammatory therapies. Curr Pharm Design 24: 1449-1484, 2018.
Youle et al. "Receptor-mediated uptake of an extracellular Bcl-XL fusion protein inhibits apoptosis" Proceedings of Nat'l Academy of Sciences, vol. 96, oo. 9563-9567 (1999).
Youle et al. "The Cytokine, Granulocyte-Macrophage Colony-stimulating Factor (GM-CSF), Can Deliver Bel-XL as an Extracellular Fusion Protein to Protect Cells from Apoptosis and Retain

(56) References Cited

OTHER PUBLICATIONS

Differentiation Induction" The Journal of Biological Chemistry, vol. 282, No. 15, pp. 11246-11254 (2007).
Youle et al., "The BCL-2 protein family: opposing activities that mediate cell death", Nature Reviews, vol. 9, pp. 47-59 (2008).
ISR and WO issued in PCT/US2013/054164 on May 7, 2014.
ISR issued in PCT/US2017/066529 on Apr. 9, 2018, and IPRP issued in PCT/US2017/066529 on Jun. 18, 2019.
Bhattacharya et al. Impact of genetic variation on three dimensional structure and function of proteins. PLoS ONE 12(3): e0171355, 2017.
Bork, P. Powers and pitfalls in sequence analysis: the 70% hurdle. Genome Res 10: 398-400, 2000.
Brenner. S.E. Errors in genome annotation. Trends in Genetics 15:132-133, 1999.
Chen et al. Fusion protein linkers: property, design, and functionality. Adv Drug Rev 65: 1357-1369, 2013 (online Sep. 29, 2012).
Doerks et al. Protein annotation: detective work for function prediction. Trends in Genetics 14:248-250, 1998.
Fenton et al. Rheostat positions: a new classification of protein positions relevant to pharmacogenomics. Medicinal Chem Res 29:1133-1146, 2020.
Gardai et al. Phosphorylation of Bax Ser184 by Akt regulates its activity and apoptosis in neutrophils. J Biol Chem 279(20): 21085-21095, 2004.
Guo et al. Protein tolerance to random amino acid change. Proc Natl Acad Sci USA 101 (25): 9205-9210, 2004.
Ngo et al. "Computational complexity, protein structure prediction, and the Levinthal paradox" in The Protein Folding Problem and Tertiary Structure Prediction, pp. 492-495, 1994.
Skolnick et al. From genes to protein structure and function: novel applications of computational approaches in the genomic era. Trends Biotechnol 18(1) :34-39 2000.
Smith et al. The challenges of genome sequence annotation or "the devil is in the details". Nature Biotechnol 15: 1222-1223, 1997.
Tokuriki et al. Stability effects of mutations and protein evolvability. Curr Opin Structural Biol 19: 596-604, 2009.
Wang et al. Mono- or double-site phosphorylation distinctly regulates the proapoptotic function of Bax. PLoS One 5(10): e13393, 2010 (8 total pages).
Wells, J.A. Additivity of mutational effects in proteins. Biochemistry 29(37): 8509-8517, 1990.
Oka K, Yamamoto M, Nonaka T, Tomonaga M. The significance of artificial cerebrospinal fluid as perfusate and endoneurosurgery. Neurosurgery.Apr. 1996;38(4):733-6. PMID: 8692392.
ISR/WO issued in PCT/IB2018/001284 on Mar. 11, 2019.
Kazunari et al. Neurosurgery 38(4):p. 733-736, Apr. 1996.
ISR/WO issued in PCT/IB2019/000759 on Jan. 20, 2020.
ISR/WO issued in PCT/CA2020/000013 on May 15, 2020.
Suzuki, Akiko et al. "Targeting of IL-4 and IL-13 receptors for cancer therapy." Cytokine vol. 75,1 (2015): 79-88. doi:10.1016/j.cyto.2015.05.026.
Post, Dawn E., et al. "Local delivery of the anti-tumorigenic interleukin-4 (IL-4) cytokine to tumors using an oncolytic adenovirus." Cancer Res May 1, 2005; 65 (9_Supplement): 317.
Sosman, J A et al. "A phase I trial of continuous infusion interleukin-4 (IL-4) alone and following interleukin-2 (IL-2) in cancer patients." Annals of oncology : official journal of the European Society for Medical Oncology vol. 5,5 (1994): 447-52. doi: 10.1093/oxfordjournals.annonc.a058878.
Ding et al., Convection-enhanced Delivery of Free Gadolinium with the Experimental Chemotherapeutic Agent PRX321., Neurol Res. Oct. 2010; 32(8): 810-815.
Weber et al., Safety, tolerability, and tumor response of IL4-Pseudomonas exotoxin (NBI-3001) in patients with recurrent malignant glioma., J Neurooncol. Aug.-Sep. 2003;64(1-2):125-37. doi: 10.1007/BF02700027.
Thaci et al., "Significance of interleukin-13 receptor alpha 2-targeted glioblastoma therapy," Neuro Oncol. Oct. 2014;16(10):1304-12.
ISR/WO issued in PCT/CA2021/051433 on Jan. 12, 2022.
Sampson et al., "MDNA55, a Locally Administered IL4 Guided Toxin for Targeted Treatment of Recurrent Glioblastoma Shows Long Term Survival Benefit," European Journal of Cancer (2020). 138. S6. 10.1016/S0959-8049(20)31084-4.
Medicenna, "Convection-Enhanced Delivery (CED) of MDNA55 in Adults With Recurrent or Progressive Glioblastoma," Clinical Trial NCT02858895, First posted Aug. 8, 2016. (https://clinicaltrials.gov/study/NCT02858895).
Bautz, "Medicenna Therapeutics Corp.," Zacks Small-Cap Research, May 14, 2019 (May 14, 2019), acquired from: http://s27.q4cdn.com/906368049/files/News/2019/Zacks_SCR_Research_05142019_T.MDNA_Bautz.pdf.
Yu et al., "Efficacy and safety of bevacizumab for the treatment of glioblastoma," Exp Ther Med. Feb. 2016;11(2):371-380.
Gramatzki et al., "Bevacizumab may improve quality of life, but not overall survival in glioblastoma: an epidemiological study," Ann Oncol. Jun. 1, 2018;29(6):1431-1436.
ISR/WO issued in PCT/IB2023/000132 on Oct. 13, 2023.
Anonymous: "Medicenna Reports Compelling Results from Recurrent Glioblastoma Trial When Compared to an Eligibility-Matched Control Arm", Jan. 13, 2020 (Jan. 13, 2020), XP093209969, Retrieved from the Internet: URL:https://ir.medicenna.com/node/6776/pdf [retrieved on Sep. 30, 2024] *abstract*.
Anonymous John H. et al: "MDNA55 survival in recurrent glioblastoma (rGBM) patients express ing the interleukin-4 receptor (IL4R) as compared to a matched synthetic control. Journal of Clinical Oncology", Journal of Clinical Oncology, vol. 38, No. 15_ suppl, May 20, 2020 (May 20, 2020), pp. 2513-2513, XP093209976, ISSN: 0732-183X, DOI: 10.1200/JCO.2020.38. 15_ suppl . 2513, Retrieved from the Internet: URL: https://ascopubs.org/ doi/10.1200/ JCO.2, 020.38.IS_suppl.2513> *abstract*.
Kawakami et al., Structure, Function, and Targeting of Interleukin 4 Receptors on Human Head and Neck Cancer Cells., Cancer Research, 60, 2981-2987, Jun. 1, 2000.
Arshad et al., Convection-Enhanced Delivery of Carboplatin PLGA Nanoparticles for the Treatment of Glioblastoma., 2015, PLoS ONE 10(7): e0132266. doi: 10.1371/journal.
Fiandaca et al., The Use of Convection-Enhanced Delivery with Liposomal Toxins in Neurooncology., Toxins 2011, 3, 369-397; doi: 10.3390/toxins3040369.

* cited by examiner

| Avastin Use | mOS (months) |
|---|---|
| Yes | 11.9 |
| No | 7.8 |

Log-rank p-value = 0.01577

| Avastin Use | mOS (months) | OS-6 (n=18) | OS-9 (n=17) | OS-12 |
|---|---|---|---|---|
| Yes | undef | 78% | 78% | n=4 |
| No | 6.0 | 40% | 0% | Not reached |

6 and 9 µg/mL Cohorts only

| Group | N | mOS (months) | OS-12 |
|---|---|---|---|
| On-Study Avastin Use | 8 | 18.3 | 63% |
| No Avastin Use | 7 | 6.0 | 43% |

| Comparison | HR | 95% CI | |
|---|---|---|---|
| On-study Avastin / No Avastin | 0.38 | 0.11 | 1.39 |

COMBINATION THERAPY OF MDNA55 AND A VASCULAR ENDOTHELIAL GROWTH FACTOR A (VEGF-A)

CROSS REFERENCE TO RELATED APPLICATIONS

This application is a U.S. National Phase Application under 35 U.S.C. § 371 of International Application No. PCT/CA2021/051433, filed Oct. 12, 2021, entitled "COMBINATION THERAPY OF MDNA55 AND A VASCULAR ENDOTHELIAL GROWTH FACTOR A (VEGF-A)", which claims priority to U.S. Provisional Patent Application No. 63/090,663, filed Oct. 12, 2020, entitled "COMBINATION THERAPY OF CENTRAL NERVOUS SYSTEM TUMORS", each of which is hereby incorporated by reference in its entirety.

BACKGROUND

First-line treatment for primary glioblastoma (GB, sometimes referred to as glioblastoma multiforme (GBM)) includes surgical resection of the bulk tumor to the maximal extent possible consistent with neurological preservation, followed by the Stupp protocol, which is established as the standard of care for newly diagnosed GB (Stupp et al., 2005).

Using current treatment paradigms, most GB patients experience tumor recurrence/progression after standard first line treatment. Treatment options for patients with recurrent GB are very limited and the outcome is generally unsatisfactory. Specifically, chemotherapy regimens for recurrent or progressive GB have been unsuccessful, producing toxicity without benefit (Weller et al., 2013). This is mainly due to the lack of tissue specificity with resultant toxicity to normal tissues and consequently, a narrow therapeutic index. As overall survival remains dismal, novel anti-cancer modalities, with greater tumor specificity, more robust cytotoxic mechanisms and novel delivery techniques are needed for the treatment of recurrent GB.

Treatment options for patients with recurrent or progressive GB are very limited and positive long-term outcomes are rare. Drugs currently approved in the US for treatment of recurrent GB are Gliadel®, and bevacizumab (Avastin®). Bevacizumab (also referred to as Avastin) is a humanized monoclonal IgG antibody that inhibits angiogenesis by binding and neutralizing VEGF-A.

Avastin® is an anti-angiogenic antibody that targets the vascular endothelial growth factor (VEGF) receptors. It is indicated as a single agent for adult patients with recurrent GB (New Drug Application No. 125085; approval date: Feb. 26, 2004) but has not been shown to improve disease-related symptoms or survival. Avastin® was approved on the basis of objective response rate (ORR of 26%) endpoint (Genentech 2016; Cohen et al., 2009; Freidman et al., 2009). In 2013, Avastin® completed its confirmatory trial in newly diagnosed GB patients and did not meet its primary endpoint of overall survival. Based on the results of this trial, Genentech did not receive approval in the European Union (EU) for newly diagnosed GB; however, Avastin® remains indicated in the US and Japan for recurrent GB. Several studies have since compared efficacy with Avastin® or assessed combination approaches.

MDNA55 is a targeted immunotoxin consisting of a bioengineered circularly permuted version of interleukin-4 (cpIL-4), fused to a truncated version of a potent bacterial toxin-*Pseudomonas aeruginosa* exotoxin (PE) A, comprising the PE catalytic domain (Kreitman et al., 1994). MDNA55 binds to interleukin-4 receptors (IL-4R) expressed on the surface of cells whereupon the entire complex is endocytosed. Following cleavage and activation by furin-like proteases found in high concentrations in the endosome of cancer cells, the catalytic domain of the truncated PE is released into the cytosol where it induces cell death via ADP-ribosylation of the Elongation Factor-2 and induction of apoptosis through caspase activation (Wedekind et al., 2001). Cells that do not express the IL-4R target do not bind to MDNA55 and are therefore, not subject to PE-mediated cell death. The PE portion was engineered to retain the catalytic domain but not the cell-binding domain.

Glioblastoma is a rapidly progressing and near-universally fatal cancer that is devastating to patients. This aggressive type of brain cancer is associated with substantial morbidity, often in the form of rapid deterioration of cognitive and psychomotor function, and a 1-year survival rate of approximately 25% following failure of front-line treatment (Lamborn et al., 2008). There is currently no effective treatment. MDNA55 represents a potential therapeutic advance. MDNA55 is a rationally designed targeted therapy with the potential to extend the survival of patients with GB. Combination therapy with Avastin, in particular subtherapeutic Avastin dosages, are described herein and provide an improved treatment of GB.

Ascertaining if IL-4R positive patients respond better to MDNA55 and by identifying specific patient subtypes who are most likely to respond, as provided in the present invention, will help address these outstanding issues and may lead to further improved clinical outcomes for patients. Overall, there remains a need in the art for further effective methods for the treatment of these IL-4R expressing tumors, and the combination therapy of MDNA55 with Avastin, in particular subtherapeutic Avastin dosages, described herein meets this need.

BRIEF SUMMARY

In one aspect, the disclosure of the current invention provides a method of treating a central nervous system (CNS) tumor in a subject. The method comprises administering to the subject MDNA55 (SEQ ID NO:1) in combination with a vascular endothelial growth factor A (VEGF-A) inhibitor administered at a subtherapeutic level, wherein the VEGF-A inhibitor is administered at least two weeks apart from the MDNA55. In another aspect, the disclosure of the current invention provides a method of inhibiting a central nervous system (CNS) tumor in a subject that is characterized by high level of an IL-4 receptor (IL-4R) expression. The method comprises contacting the CNS tumor with MDNA55, and contacting the CNS tumor with a subtherapeutic level of vascular endothelial growth factor A (VEGF-A) inhibitor at least two weeks apart from contact with the MDNA55. In another aspect, the disclosure of the current invention provides a method for predicting or determining the efficacy of treatment with MDNA55 in combination with a vascular endothelial growth factor A (VEGF-A) inhibitor. The method comprises (a) measuring the level of IL-4 receptor (IL-4R) expression in a biological sample obtained from a CNS tumor in a subject; (b) quantitating the measurement of the level of IL-4R expression in the biological sample; and (c) correlating the level of IL-4R with the efficacy of treatment, wherein a moderate or high level of IL-4R expression is indicative of treatment efficacy for treatment with the MDNA55 in combination with a subtherapeutic level of the vascular endothelial growth factor A (VEGF-A) inhibitor, wherein the VEGF-A inhibitor is administered at least two weeks apart from the MDNA55.

In some embodiments, the subject has a recurrent CNS tumor or a newly diagnosed CNS tumor. In some embodiments, the subject has an IL-4R positive CNS tumor. In some embodiments, the CNS tumor is selected from the group consisting of glioma, glioblastoma, astrocytoma, medulloblastoma, craniopharyngioma, ependymoma, pinealoma, hemangioblastoma, acoustic neuroma, oligodendroglia, meningioma, meningioma, neuroblastoma, and retinoblastoma. In some embodiments, the CNS tumor is a glioblastoma. In some embodiments, the CNS tumor is a recurrent or refractory glioblastoma.

In some embodiments, the vascular endothelial growth factor A (VEGF-A) inhibitor is bevacizumab (Avastin®) or a biosimilar of bevacizumab.

In some embodiments, the MDNA55 is administered at least two weeks from the vascular endothelial growth factor A (VEGF-A) inhibitor.

In some embodiments, the high level of IL-4R expression is indicated by a percent score of ≥2+. In some embodiments, the high level of IL-4R expression is indicated by a percent score of ≥3+. In some embodiments, the moderate level of IL-4R expression is indicated by a percent score of ≥1+ but <2+. In some embodiments, the moderate level of IL-4R expression is indicated by H-Scores from 76 to 150. In some embodiments, the high level of IL-4R expression is indicated by H-Scores from 151 to 225. In some embodiments, the high level of IL-4R expression is indicated by H-Scores from 226 to 300.

In some embodiments, the level of IL-4R expression is measured by measuring the level of IL-4Rα expression. In some embodiments, the level of IL-4R expression is the level of Type 2 IL-4R (Type II IL-4R, comprising IL4Rα and IL13Rα1) expression. In some embodiments, the level of IL-4R expression is measured using immunohistochemical (IHC) staining for IL-4R, including IL-4Rα expression.

In some embodiments, the MDNA55 is administered as a single dose of about 90 μg (1.5 μg/mL in 60 mL), about 180 μg (4.5 μg/mL in 40 mL or 3 μg/mL in 60 mL) about 240 μg (6 μg/mL in 40 mL or 4 μg/mL in 60 mL). In some embodiments, the MDNA55 is administered at a dosage of about 1.5 μg/mL in 60 mL. In some embodiments, the MDNA55 is administered at a dosage of about 6 μg/mL in 40 mL. In some embodiments, the MDNA55 is administered at a dosage of about 4 μg/mL in 60 mL. In some embodiments, the MDNA55 is administered as a single dose of about 1.5 μg/mL to about 6 μg/mL.

In some embodiments, the MDNA55 is administered intratumorally. In some embodiments, the intratumoral administration comprises intracranial administration.

In some embodiments, the MDNA55 is formulated in an artificial cerebral spinal fluid (CSF) solution and albumin, wherein the formulation is co-administered with a surrogate tracer to a subject in need thereof. In some embodiments, the surrogate tracer is magnetic resonance imaging (MRI) contrast agent. In some embodiments, the surrogate tracer is a gadolinium-bound tracer. In some embodiments, the surrogate tracer is selected from the group consisting of gadolinium-diethylenetriamine pentaacetic acid (Gd-DTPA) and gadolinium-bound albumin (Gd-albumin).

In some embodiments, the MDNA55 is administered via an intracranial catheter. In some embodiments, the MDNA55 is administered by convection-enhanced delivery (CED). In some embodiments, the MDNA55 is administered as a single dose via convection-enhanced delivery (CED). In some embodiments, the MDNA55 is administered via one or more intracranial catheters, including 1 to 3 catheters. In some embodiments, the MDNA55 is administered through the catheter with a flow rate of about 5 μL/min/catheter to about 20 μL/min/catheter or a flow rate of about 15 μL/min/catheter. In some embodiments, the MDNA55 is administered through the catheter at a concentration of about 1.5 μg/mL and with a flow rate of about 15 μL/min/catheter.

In some embodiments, the subtherapeutic dose of the VEGF-A inhibitor is below about 10 mg/kg. In some embodiments, the VEGF-A inhibitor is bevacizumab or a biosimilar of bevacizumab and the subtherapeutic dose of the VEGF-A inhibitor is at or below about 7.5 mg/kg. In some embodiments, the VEGF-A inhibitor is bevacizumab or a biosimilar of bevacizumab and the subtherapeutic dose of the VEGF-A inhibitor is from about 5 mg/kg to 7.5 mg/kg. In some embodiments, the VEGF-A inhibitor is bevacizumab or a biosimilar of bevacizumab and the subtherapeutic dose of the VEGF-A inhibitor is at or below 5 mg/kg.

In some embodiments, the MDNA55 is administered at a dose of about 240 μg (6 μg/mL in 40 mL or 4 μg/mL in 60 mL) and the subtherapeutic dose of bevacizumab or a biosimilar of bevacizumab is administered at least two weeks apart from the MDNA55. In some embodiments, the MDNA55 is administered at a dose of about 240 μg (6 μg/mL in 40 mL or 4 μg/mL in 60 mL) and the subtherapeutic dose of bevacizumab or a biosimilar of bevacizumab is administered at least three weeks apart from the MDNA55. In some embodiments, the MDNA55 is administered at a dose of about 240 μg (6 μg/mL in 40 mL or 4 μg/mL in 60 mL) and the subtherapeutic dose of bevacizumab or a biosimilar of bevacizumab is administered at least four weeks apart from the MDNA55.

In some embodiments, the VEGF-A inhibitor is administered before the MDNA55. In some embodiments, the VEGF-A inhibitor is administered after the MDNA55.

In some embodiments, the VEGF-A inhibitor is administered at about 5 mg/kg, and administered at least two weeks apart from the MDNA55. In some embodiments, the VEGF-A inhibitor is administered at about 7.5 mg/kg, and administered at least three weeks apart from the MDNA55. In some embodiments, the VEGF-A inhibitor is administered at about 7.5 mg/kg, and administered at least four weeks apart from the MDNA55.

In some embodiments, the MDNA55 is administered at a dose of about 240 μg, and the VEGF-A inhibitor is administered at least two weeks apart from the MDNA55 and at a dose about 5 mg/kg. In some embodiments, the MDNA55 is administered at a dose of about 240 μg, and the VEGF-A inhibitor is administered at least three weeks apart from the MDNA55 and at a dose about 7.5 mg/kg. In some embodiments, the MDNA55 is administered at a dose of about 240 μg, and the VEGF-A inhibitor is administered at least four weeks apart from the MDNA55 and at a dose about 7.5 mg/kg.

In some embodiments, the MDNA55 is administered at a dose below 240 μg, and the VEGF-A inhibitor is administered at least two weeks apart from the MDNA55 and at a dose about 5 mg/kg. In some embodiments, the MDNA55 is administered at a dose below 240 μg, and the VEGF-A inhibitor is administered at least three weeks apart from the MDNA55 and at a dose about 7.5 mg/kg. In some embodiments, the MDNA55 is administered at a dose of below 240 μg, and the VEGF-A inhibitor is administered at least four weeks apart from the MDNA55 and at a dose about 7.5 mg/kg.

In some embodiments, the VEGF-A inhibitor is administered at least two weeks apart from the MDNA55 for a period of at least 12 weeks, 16 weeks, 20 weeks, 24 weeks, 30 weeks, 36 weeks, 40 weeks, 44 weeks, 48 weeks, or 52 weeks or more. In some embodiments, the VEGF-A inhibitor is administered at least three weeks apart from the MDNA55 for a period of at least 12 weeks, 16 weeks, 20 weeks, 24 weeks, 30 weeks, 36 weeks, 40 weeks, 44 weeks, 48 weeks, or 52 weeks or more. In some embodiments, the VEGF-A inhibitor is administered at least four weeks apart from the MDNA55 for a period of at least 12 weeks, 16 weeks, 20 weeks, 24 weeks, 30 weeks, 36 weeks, 40 weeks, 44 weeks, 48 weeks, or 52 weeks or more.

In some embodiments, the MDNA55 is administered through the catheter with a flow rate of about 3 μL/min/catheter to about 10 μL/min/catheter.

In some embodiments, the MDNA55 is formulated according to the formulation provided in Table 3.

In some embodiments, the biosimilar of bevacizumab is selected from the group consisting of bevacizumab-awwb (Mvasi), bevacizumab-bvzr (Zirabev), Aybintio (SB8), MYL-14020 (Abevmy), FKB238 (AstraZeneca/Fujifilm Kyowa Kirin Biologics), BCD-021, BCD500, Krabeva, BAT1706, BI 695502, CT-P16, CHS-5217, DRZ_BZ, Lumiere, Cizumab, IBI-305, MIL60, Bevax (BEVZ92), ONS-1045, HD204, Bevacirel, HLX04, and TX16.

Another aspect of the current disclosure is directed to a unit dosage formulation for treating a central nervous system (CNS) tumor in a subject. The formulation comprises MDNA55 formulated from about 1.5 μg/mL to about 6 μg/mL in 15 ml to 200 ml and wherein the MDNA55 is administered at least two weeks apart from a vascular endothelial growth factor A (VEGF-A) inhibitor administered at a subtherapeutic level.

In some embodiments, the VEGF-A inhibitor is administered at least three weeks apart from the MDNA55. In some embodiments, the VEGF-A inhibitor is administered at least four weeks apart from the MDNA55. In some embodiments, the VEGF-A inhibitor is administered before the MDNA55. In some embodiments, the VEGF-A inhibitor is administered after the MDNA55.

In some embodiments, the MDNA55 is formulated at about 6 μg/mL in 40 ml or about 4 μg/mL in 60 ml, and the VEGF-A inhibitor is bevacizumab or a biosimilar of bevacizumab administered at from about 5 mg/kg to 7.5 mg/kg. In some embodiments, the MDNA55 is formulated at about 6 μg/mL in 40 ml or about 4 μg/mL in 60 ml, and the VEGF-A inhibitor is bevacizumab or a biosimilar of bevacizumab administered at about 5 mg/kg two weeks apart from the MDNA55. In some embodiments, the MDNA55 is formulated at about 6 μg/mL in 40 ml or about 4 μg/mL in 60 ml, and the VEGF-A inhibitor is bevacizumab or a biosimilar of bevacizumab administered at about 7.5 mg/kg three weeks apart from the MDNA55.

In some embodiments, the MDNA55 and/or VEGF-A inhibitor is administered via one or more intracranial catheters, including 1 to 3 catheters. In some embodiments, the MDNA55 is administered through the catheter with a flow rate of about 3 μL/min/catheter to about 10 μL/min/catheter.

In some embodiments, the MDNA55 is administered intratumorally. In some embodiments, the intratumoral administration comprises intracranial administration.

In some embodiments, the MDNA55 formulation is in an artificial cerebral spinal fluid (CSF) solution and albumin, wherein the formulation is co-administered with an optional surrogate tracer to a subject in need thereof. In some embodiments, the optional surrogate tracer is magnetic resonance imaging (MRI) contrast agent. In some embodiments, the optional surrogate tracer is a gadolinium-bound tracer. In some embodiments, the optional surrogate tracer is selected from the group consisting of gadolinium-diethylenetriamine pentaacetic acid (Gd-DTPA) and gadolinium-bound albumin (Gd-albumin).

In some embodiments, the MDNA55 and/or VEGF-A inhibitor is administered via an intracranial catheter. In some embodiments, the MDNA55 and/or VEGF-A inhibitor is administered by convection-enhanced delivery (CED). In some embodiments, the MDNA55 and/or VEGF-A inhibitor is administered as one or more dosages via convection-enhanced delivery (CED). In some embodiments, the MDNA55 and/or VEGF-A inhibitor is administered as a single dose via convection-enhanced delivery (CED).

In some embodiments, the unit dosage formulation comprises the formulation in Table 3.

In some embodiments, the biosimilar of bevacizumab is selected from the group consisting of bevacizumab-awwb (Mvasi), bevacizumab-bvzr (Zirabev), Aybintio (SB8), MYL-14020 (Abevmy), FKB238 (AstraZeneca/Fujifilm Kyowa Kirin Biologics), BCD-021, BCD500, Krabeva, BAT1706, BI 695502, CT-P16, CHS-5217, DRZ_BZ, Lumiere, Cizumab, IBI-305, MIL60, Bevax (BEVZ92), ONS-1045, HD204, Bevacirel, HLX04, and TX16.

DETAILED DESCRIPTION

Figure 1:
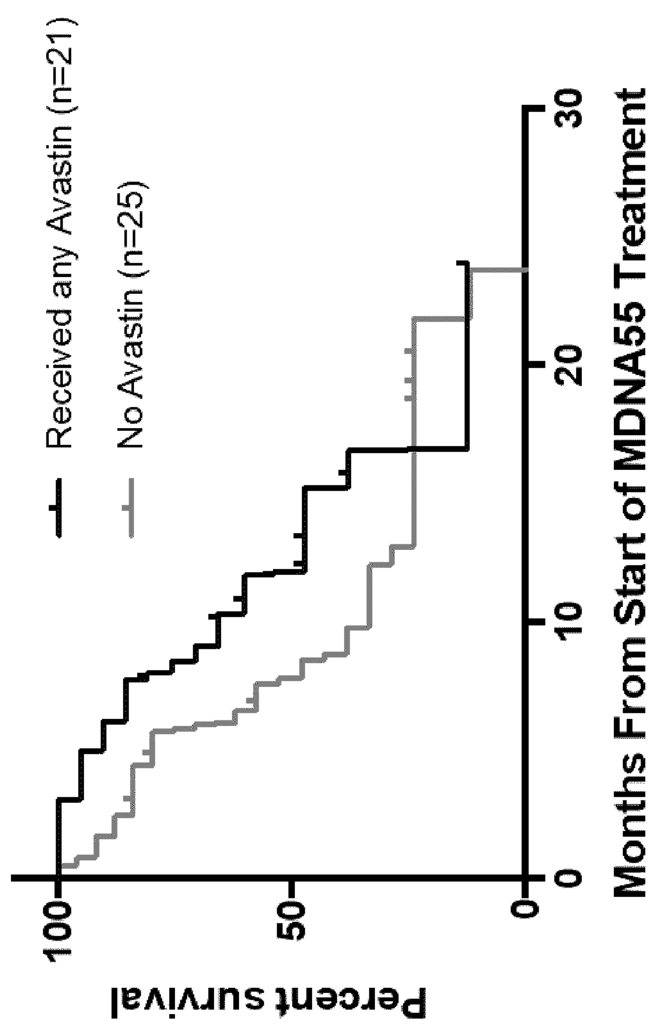
FIG. 1. Provides data regarding subjects receiving Avastin* following MDNA55 treatment show longer survival. (*Refers to subjects who received therapeutic doses of Avastin after coming off MDNA55 study.) MDNA55 was administered to patients at 6.0 μg/mL or 9.0 μg/mL and the sub-therapeutic dose of Avastin administered to the patient was between 5 mg/kg every two weeks to 7.5 mg/kg every three weeks.

In order for the present disclosure to be more readily understood, certain terms and phrases are defined below as well as throughout the specification.

MDNA55 can be optionally co-administered with a tracer (an MRI contrast agent) using convection enhanced delivery (CED) allowing real-time monitoring of drug distribution in and around the tumor. MDNA55 is a targeted immunotoxin consisting of a bioengineered circularly permuted version of interleukin-4 (cpIL-4), fused to a truncated version of a potent bacterial toxin—*Pseudomonas aeruginosa* exotoxin (PE) A comprising the PE catalytic domain (Kreitman et al., 1994). MDNA55 binds to interleukin-4 receptors (IL-4R) expressed on the surface of cells whereupon the entire complex is endocytosed. Following cleavage and activation by furin-like proteases found in high concentrations in the endosome of cancer cells, the catalytic domain of the truncated PE is released into the cytosol where it induces cell death via ADP-ribosylation of the Elongation Factor-2 and induction of apoptosis through caspase activation (Wedekind et al., 2001). Cells that do not express the IL-4R target do not bind to MDNA55 and are therefore, not subject to PE-mediated cell death.

A. Definitions

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, NY 2001); March, *Advanced Organic Chemistry Reactions, Mechanisms and Structure* 5th ed., J. Wiley & Sons (New York, NY 2001); and Sambrook and Russell, *Molecular Cloning: A Laboratory Manual* 3rd ed., Cold Spring harbor Laboratory Press (Cold Spring Harbor, N Y 2001), provide one skilled in the art with a general guide to many terms used in the present disclosure. As appropriate, procedures involving the use of commercially available kits and reagents are generally carried out in accordance with manufacturer defined protocols and/or parameters unless otherwise noted.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

Accession Numbers: Reference numbers assigned to various nucleic acid and amino acid sequences in the NCBI database (National Center for Biotechnology Information) that is maintained by the National Institute of Health, U.S.A. The accession numbers listed in this specification are herein incorporated by reference as provided in the database as of the date of filing this application.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CHI domains; (ii) an Fd fragment consisting of the VH and CHI domains; (iii) an Fv fragment consisting of the VL and VH domains of a single arm of an antibody (scFv) and scFv molecules linked to each other to form a bivalent dimer (diabody) or trivalent trimer (triabody); (iv) a dAb fragment (Ward et al., Nature 341:544-546, 1989) which consists of a VH domain; (v) an isolated complementarity determining region (CDR); and (vi) a F(ab')2 fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, Current Protocols in Immunology Wiley/Greene, N.Y., 1991; and Harlow and Lane, Antibodies: A Laboratory Manual Cold Spring Harbor Press, N Y, 1989; Stites et al., (eds.) Basic and Clinical Immunology (4th ed.) Lange Medical Publications, Los Altos, Calif, and references cited therein; Goding, Monoclonal Antibodies: Principles and Practice (2nd ed.) Academic Press, New York, N.Y., 1986; and Kohler and Milstein, Nature 256: 495-497, 1975. Other suitable techniques for antibody preparation include selection of libraries of recombinant antibodies in phage or similar vectors. See, Huse et al., Science 246: 1275-1281, 1989; and Ward et al., Nature 341: 544-546, 1989.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123: 793, 1979; Morrison et al., Ann Rev. Immunol 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), Antibody Engineering, 2nd Edition Freeman and Company, N Y, 1995; McCafferty et al., Antibody Engineering, A Practical Approach, IRL at Oxford Press, Oxford, England, 1996, and Paul Antibody Engineering Protocols Humana Press, Towata, N.J., 1995.

In some examples, an antibody specifically binds to a target protein (e.g., a cell surface receptor such as an IL4 receptor) with a binding constant that is at least $10^3$ $M^{-1}$ greater, $10^4$ $M^{-1}$ greater or $10^5$ $M^{-1}$ greater than a binding constant for other molecules in a sample. In some examples, a specific binding reagent (such as an antibody (e.g., monoclonal antibody) or fragments thereof) has an equilibrium constant ($K_d$) of 1 nM or less. For example, a specific binding agent may bind to a target protein with a binding affinity of at least about $0.1\times10^{-8}$ M, at least about $0.3\times10^{-8}$ M, at least about $0.5\times10^{-8}$ M, at least about $0.75\times10^{-8}$ M, at least about $1.0\times10^{-8}$ M, at least about $1.3\times10^{-8}$ M at least about $1.5\times10^{-8}$ M, or at least about $2.0\times10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Binds or binding: The association between two or more molecules, wherein the two or more molecules are in close physical proximity to each other, such as the formation of a complex. An exemplary complex is a receptor-ligand pair or an antibody-antigen pair. Generally, the stronger the binding of the molecules in a complex, the slower their rate of dissociation. Specific binding refers to a preferential binding between an agent and a specific target. Such binding can be a specific noncovalent molecular interaction between the ligand and the receptor.

Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Cancer: Malignant neoplasm that has undergone characteristic anaplasia with loss of differentiation, increased rate of growth, invasion of surrounding tissue, and is capable of metastasis. Residual cancer is cancer that remains in a subject after any form of treatment given to the subject to reduce or eradicate a cancer and recurrent cancer is cancer that recurs after such treatment. Metastatic cancer is a cancer at one or more sites in the body other than the site of origin of the original (primary) cancer from which the metastatic cancer is derived. In the case of a metastatic cancer originating from a solid tumor, one or more (for example, many) additional tumor masses can be present at sites near or distant to the site of the original tumor. The phrase “disseminated metastatic nodules” or “disseminated metastatic tumors” refers to a plurality (typically many) metastatic tumors dispersed to one or more anatomical sites. For example, disseminated metastatic nodules within the peritoneum (that is a disseminated intraperitoneal cancer) can arise from a tumor of an organ residing within or outside the peritoneum, and can be localized to numerous sites within the peritoneum. Such metastatic tumors can themselves be discretely localized to the surface of an organ, or can invade the underlying tissue.

Decrease: To reduce the quality, amount, or strength of something. In one example, a therapy (such as treatment with MDNA55) decreases a cancer stem cell population (such as by decreasing the size of a tumor, the volume of a tumor, the metastasis of a tumor, the number of cancer cells and/or cancer stem cells, or combinations thereof), or one or more symptoms associated with cancer, for example as compared to the response in the absence of the therapy. In a particular example, a therapy decreases the size of a tumor, volume of a tumor, number of cancer cells and/or cancer stem cells, or the metastasis of a cancer, or combinations thereof, subsequent to the therapy, such as a decrease of at least about 10%, at least about 20%, at least about 50%, or even at least about 90%. Such decreases can be measured using the methods disclosed herein.

Diagnose: The process of identifying a medical condition or disease, for example from the results of one or more diagnostic procedures. In particular examples, includes determining the prognosis of a subject (e.g., likelihood of survival over a period of time, such as likelihood of survival in 6-months, 1-year, or 5-years). In a specific example, cancer is diagnosed by detecting the presence of a cancer stem cell in a sample using one or more of the targets on the cancer stem cell surface. For example, diagnoses can include determining the particular stage of cancer or the presence of a site of metastasis.

Linker: A molecule used to connect one or more agents to one or more other agents. For example, a linker can be used to connect one or more cargo moieties to one or more targeting moieties. Particular non-limiting examples of linkers include dendrimers, such as synthetic polymers, peptides, proteins and carbohydrates. Linkers additionally can contain one or more protease cleavage sites or be sensitive to cleavage via oxidation and/or reduction.

Pharmaceutically acceptable carriers: The term “pharmaceutically acceptable carriers” refers to pharmaceutically acceptable carriers (vehicles) useful in this disclosure are conventional. Remington’s Pharmaceutical Sciences, by E. W. Martin, Mack Publishing Co., Easton, Pa., 15th Edition (1975), describes compositions and formulations suitable for pharmaceutical delivery of one or more therapeutic or diagnostic agents, such as MDNA55 provided herein.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Pharmaceutical agent or drug: A chemical compound or composition capable of inducing a desired therapeutic effect when administered to a subject, alone or in combination with another therapeutic agent(s) or pharmaceutically acceptable carriers. In a particular example, a pharmaceutical agent (such as MDNA55) treats a cancer, for example by reducing the size of the tumor (such as the volume or reducing the number of cancer cells and/or cancer stem cells), reducing metastasis of the cancer, or combinations thereof.

Recombinant: A recombinant molecule (such as a recombinant nucleic acid molecule or protein) has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein.

Sample: Biological specimens such as samples containing biomolecules, such as nucleic acid molecules, proteins, or both. Exemplary samples are those containing cells or cell lysates from a subject, such as those present in peripheral blood (or a fraction thereof such as serum), urine, saliva, tissue biopsy, cheek swabs, surgical specimen, fine needle aspirates, cervical samples, and autopsy material. In a specific example, a sample is obtained from a tumor (for example a section of tissue from a biopsy), which can include tumor cells that are both non-cancer cells and/or cancer stem cells and cancer cells and/or cancer stem cells. In some embodiments, the tumor sample is from a central nervous system (CNS) tumor.

Sequence identity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN can be used to compare nucleic acid sequences, while BLASTP can be used to compare amino acid sequences. To compare two nucleic acid sequences, the options can be set as follows: –i is set to a file containing the first nucleic acid sequence to be compared (such as C:\seq1.txt); —j is set to a file containing the second nucleic acid sequence to be compared (such as C:\seq2.txt); —p is set to blastn; —o is set to any desired file name (such as C:\output.txt); —q is set to —l; —r is set to 2; and all other options are left at their default setting. For example, the following command can be used to generate an output file containing a comparison between two sequences: C:\B12seq —i c:\seq1.txt —j c:\seq2.txt —p blastn —o c:\output.txt —q —l —r 2.

To compare two amino acid sequences, the options of B12seq can be set as follows: –i is set to a file containing the first amino acid sequence to be compared (such as C:\seq1.txt); —j is set to a file containing the second amino acid sequence to be compared (such as C:\seq2.txt); —p is set to blastp; —o is set to any desired file name (such as C:\output.txt); and all other options are left at their default setting. For example, the following command can be used to generate an output file containing a comparison between two amino acid sequences: C:\B12seq —i c:\seq1.txt —j c:\seq2.txt —p blastp —o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a sequence provided herein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a cargo moiety or targeting moiety provided herein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Subject: Living multi-cellular vertebrate organisms, a category that includes human and non-human mammals (such as laboratory or veterinary subjects).

MDNA55 is provided as SEQ ID NO:1.

```
                                    (SEQ ID NO: 1)
MDTTEKETFCRAATVLRQFYSHHEKDTRCLGATAQQFHRH

KQLIRFLKLRDRNLWGLAGLNSCPVKEANQSTLENFLERL

KTIMREKYSKCSSGGNGGHKCDITLQEIIKTLNSLTEQKT

LCTELTVTDIFAASKASGGPEGGSLAALTAHQACHLPLET

FTRHRQPRGWEQLEQCGYPVORLVALYLAARLSWNQVDQV

IRNALASPGSGGDLGEAIREQPEQARLALTLAAAESERFV

RQGTGNDEAGAANGPADSGDALLERNYPTGAEFLGDGGDV

SFSTRGTQNWTVERLLQAHROLEERGYVFVGYHGTFLEAA

QSIVEGGVRARSQDLDAIWRGFYIAGDPALAYGYAQDQEP

DARGRIRNGALLRVYVPRSSLPGFYRTSLTLAAPEAAGEV

ERLIGHPLPLRLDAITGPEEEGGRLETILGWPLAERTVVI

PSAIPTDPRNVGGDLDPSSIPDKEQAISALPDYASQPGKP

PKDEL
```

Targets on cancer cells and/or cancer cells and/or cancer stem cells include small molecules displayed on the surface of cancer cells and/or cancer stem cells. Antibodies directed to such targets can be used as targeting moieties as well as the natural ligands of the targets and derivatives thereof.

Therapeutic agents can be administered in a single dose, or in several doses, for example weekly, monthly, or bi-monthly, during a course of treatment. However, the effective amount of can be dependent on the source applied, the subject being treated, the severity and type of the condition being treated, and the manner of administration.

In one example, it is an amount sufficient to partially or completely alleviate symptoms of cancer in a subject. Treatment can involve only slowing the progression of the cancer temporarily, but can also include halting or reversing the progression of the cancer permanently. For example, a pharmaceutical preparation can decrease one or more symptoms of the cancer (such as the size of a tumor or the number of tumors or number of cancer cells and/or cancer stem cells), for example decrease a symptom by at least about 20%, at least about 50%, at least about 70%, at least about 90%, at least about 98%, or even at least about 100%, as compared to an amount in the absence of the therapeutic preparation.

Tumor: Is a neoplasm or an abnormal mass of tissue that is not inflammatory, which arises from cells of preexistent tissue. A tumor can be either benign (noncancerous) or malignant (cancerous). Examples of hematological tumors include, but are not limited to: central nervous system (CNS) cancers or tumors. Examples of solid tumors, such as sarcomas and carcinomas, include, but are not limited to brain tumors, and CNS tumors (such as a glioma, glioblastoma, astrocytoma, medulloblastoma, craniopharyngioma, ependymoma, pinealoma, hemangioblastoma, acoustic neuroma, oligodendroglioma, meningioma, meningioma, neuroblastoma and retinoblastoma). Tumors include recurrent and/or refractory CNS tumors.

Refractory: A disease or condition which does not respond to attempted forms of treatment, for example a tumor that does not respond to the standard treatment methods.

As used herein, the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasm" are used to refer to malignancies of the various organ systems, including those affecting the lung, breast, thyroid, lymph glands and lymphoid tissue, reproductive systems, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus. Cancers generally can include prostate cancer, ovarian cancer, breast cancer, endometrial cancer, multiple myeloma, melanoma, lymphomas, lung cancers including small cell lung cancer, kidney cancer, colorectal cancer, pancreatic cancer, gastric cancer, and brain cancer.

The term "carcinoma" is art-recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures.

As used herein, the term "hematopoietic neoplastic disorders" refers to diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGL), Hodgkin's disease and Reed-Stemberg disease.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease. A therapeutically effective amount can be an amount that reduces tumor number, tumor size, and/or increases survival.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. A "pharmaceutically acceptable carrier" can include, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

Unit dose used herein refers to a physically discrete unit containing a predetermined quantity of an active material (such as MDNA55) calculated to individually or collectively produce a desired effect such as a therapeutic effect. A single unit dose or a plurality of unit doses can be used to provide the desired effect, such as a therapeutic effect. The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, the therapeutic effect is to reduce tumor number. In some embodiments, the therapeutic effect is to reduce tumor size. In some embodiments, the therapeutic effect is to increase survival.

In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. IL-4 muteins in combination with anti-PD-1 antibodies, and pharmaceutical compositions thereof can be packaged in a single or multiple unit dosage form for ease of administration and uniformity of dosage.

A "therapeutically effective amount" used herein refers to an amount of an agent that alone, or together with a pharmaceutically acceptable carrier or one or more additional therapeutic agents, induces the desired response. "Therapeutically effective amount" will fall in a relatively broad range determinable through experimentation and/or clinical trials. For example, for in vivo injection, e.g., injection directly into the tissue or vasculature of a subject (for example, liver tissue or veins). Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome. In some embodiments, the effective amount is an amount sufficient to reduce tumor number. In some embodiments, the effective amount is an amount sufficient to reduce tumor size. In some embodiments, the effective amount is an amount sufficient to increase survival.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

B. Exemplary Cargo Moiety/Targeting Moiety Combinations

1. MDNA55

MDNA55 has been developed for the treatment of recurrent/progressive glioblastoma (GB). Using current treatment paradigms, most GB patients experience tumor recurrence/progression after standard first line treatment. Treatment options for patients with recurrent GB are very limited and the outcome is generally unsatisfactory. Specifically, chemotherapy regimens for recurrent or progressive GB have been unsuccessful, producing toxicity without benefit (Weller et al., 2013). This is mainly due to the lack of tissue specificity with resultant toxicity to normal tissues and consequently, a narrow therapeutic index. As overall survival remains dismal, novel anti-cancer modalities, with greater tumor specificity, more robust cytotoxic mechanisms and novel delivery techniques are needed for the treatment of recurrent GB.

MDNA55 is a novel therapeutic that provides a targeted treatment approach whereby tumor cells are more sensitive to the toxic effects of the drug than normal cells. The target, IL-4R, is an ideal but under-exploited target for the development of cancer therapeutics, as it is frequently and intensely expressed on a wide variety of human carcinomas. Expression levels of IL-4R are low on the surface of healthy and normal cells, but increase several-fold on cancer cells. A majority of cancer biopsy and autopsy samples from adult and pediatric central nervous system (CNS) tumors, including recurrent GB biopsies, have been shown to over-express the IL-4R. There is little or no IL-4R expression in normal adult and pediatric brain tissue (Joshi, et al., 2001, CANCER RESEARCH 61, 8058-8061). This differential expression of the IL-4R provides MDNA55 a wide therapeutic window. This feature alone makes MDNA55 an ideal candidate for the treatment of recurrent GB and other CNS tumors that over-express the IL-4R. Cells that do not express the IL-4R target do not bind to MDNA55 and are, therefore, not subject to PE-mediated effects.

In some embodiments, MDNA55 is SEQ ID NO: 1:

```
MDTTEKETFCRAATVLRQFYSHHEKDTRCLGATAQQFHRH
KQLIRFLKLRDRNLWGLAGLNSCPVKEANQSTLENFLERL
KTIMREKYSKCSSGGNGGHKCDITLQEIIKTLNSLTEQKT
LCTELTVTDIFAASKASGGPEGGSLAALTAHQACHLPLET
FTRHRQPRGWEQLEQCGYPVQRLVALYLAARLSWNQVDQV
IRNALASPGSGGDLGEAIREQPEQARLALTLAAAESERFV
RQGTGNDEAGAANGPADSGDALLERNYPTGAEFLGDGGDV
SFSTRGTQNWTVERLLQAHRQLEERGYVFVGYHGTFLEAA
QSIVEGGVRARSQDLDAIWRGFYIAGDPALAYGYAQDQEP
DARGRIRNGALLRVYVPRSSLPGFYRTSLTLAAPEAAGEV
ERLIGHPLPLRLDAITGPEEEGGRLETILGWPLAERTVVI
PSAIPTDPRNVGGDLDPSSIPDKEQAISALPDYASQPGKP
PKDEL
```

II. Formulations/Compositions

Pharmaceutical compositions can include MDNA55 and one or more non-toxic pharmaceutically acceptable carriers, diluents, excipients and/or adjuvants. If desired, other active ingredients may be included in the compositions. As indicated above, such compositions are suitable for use in the treatment of cancer. The term "pharmaceutically acceptable carrier" refers to a carrier medium which does not interfere with the effectiveness of the biological activity of the active ingredients and which is not toxic to the host or patient. Representative examples are provided below.

The pharmaceutical compositions may comprise, for example, from about 1% to about 95% of MDNA55. Compositions formulated for administration in a single dose form may comprise, for example, about 20% to about 90% of MDNA55, whereas compositions that are not in a single dose form may comprise, for example, from about 5% to about 20% of MDNA55. Concentration of MDNA55 in the final formulation can be at least 1 ng/mL, such as at least 1 μg/mL or at least 1 mg/mL. For example, the concentration in the final formulation can be between about 0.01 μg/mL and about 1,000 μg/mL. In one example, the concentration in the final formulation is between about 0.01 mg/mL and about 100 mg/mL.

The composition can be a liquid solution, suspension, emulsion, sustained release formulation, or powder. The composition can be formulated as a suppository, with traditional binders and carriers such as triglycerides.

MDNA55 can be delivered along with a pharmaceutically acceptable vehicle. In one example, the vehicle may enhance the stability and/or delivery properties. Thus, the disclosure also provides for formulation of MDNA55 with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of MDNA55. Alternatively, or in addition, MDNA55 formulations can include additives to stabilize the protein in vivo, such as human serum albumin, or other stabilizers for protein therapeutics known in the art. MDNA55 formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-.beta.-cyclodextrin, gum tragacanth and gum acacia; dispersing or wetting agents such as a naturally-occurring phosphatide, for example, lecithin, or condensation products of an alkylene oxide with fatty acids, for example, polyoxyethylene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, or one or more coloring agents.

Pharmaceutical compositions can be formulated as oily suspensions by suspending the active compound(s) in a vegetable oil, for example, *arachis* oil, olive oil, sesame oil or coconut oil, or in a mineral oil such as liquid paraffin. The oily suspensions may contain a thickening agent, for example, beeswax, hard paraffin or cetyl alcohol. Compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above.

Pharmaceutical compositions can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate.

The pharmaceutical compositions containing MDNA55 can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In one example, MDNA55 could be conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7(8):2407-14, 2006).

The pharmaceutical compositions described above include MDNA55 in an amount effective to achieve the intended purpose. Thus the term "therapeutically effective dose" refers to the amount of MDNA55 that ameliorates the symptoms of cancer. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Therapeutic efficacy and toxicity can also be determined by standard pharmaceutical procedures such as, for example, by determination of the median effective dose, or ED.sub.50 (i.e. the dose therapeutically effective in 50% of the population) and the median lethal dose, or LD.sub.50 (i.e. the dose lethal to 50% of the population). The dose ratio between therapeutic and toxic effects is known as the "therapeutic index," which can be expressed as the ratio, LD.sub.50/ED.sub.50. The data obtained from cell culture assays and animal studies can be used to formulate a range of dosage for human or animal use. The dosage contained in such compositions is usually within a range of concentrations that include the ED.sub.50 and demonstrate little or no toxicity. The dosage varies within this range depending upon the dosage form employed, sensitivity of the subject, and the route of administration and the like. Exemplary dosage ranges that can be used include at least 1 ng/g tumor, at least 1 μg/g tumor, or at least 1 mg/g tumor, such as dosage ranges from about 0.01 μg/g tumor to about 50 μg/g tumor, from about 0.02 μ/g tumor to about 40 μg/g tumor, from about 0.02 μg/g tumor to about 35 μg/g tumor, 0.03 μg/g tumor to about 25 μg/g tumor, from about 0.04 μg/g tumor to about 20 μg/g tumor, from about 0.04 μg/g tumor to about 10 μg/g tumor, and from about 0.5 μg/g tumor to about 2 μg/g tumor.

MDNA55 as described herein comprises SEQ ID NO: 1:

```
MDTTEKETFCRAATVLRQFYSHHEKDTRCLGATAQQFHRH
KQLIRFLKLRDRNLWGLAGLNSCPVKEANQSTLENFLERL
KTIMREKYSKCSSGGNGGHKCDITLQEIIKTLNSLTEQKT
LCTELTVTDIFAASKASGGPEGGSLAALTAHQACHLPLET
FTRHRQPRGWEQLEQCGYPVQRLVALYLAARLSWNQVDQV
IRNALASPGSGGDLGEAIREQPEQARLALTLAAAESERFV
RQGTGNDEAGAANGPADSGDALLERNYPTGAEFLGDGGDV
SFSTRGTQNWTVERLLQAHRQLEERGYVFVGYHGTFLEAA
QSIVFGGVRARSQDLDAIWRGFYIAGDPALAYGYAQDQEP
DARGRIRNGALLRVYVPRSSLPGFYRTSLTLAAPEAAGEV
ERLIGHPLPLRLDAITGPEEEGGRLETILGWPLAERTVVI
PSAIPTDPRNVGGDLDPSSIPDKEQAISALPDYASQPGKP
PKDEL
```

MDNA55 has also been described in US Patent Publication NO. 2016/0271231, incorporated by reference herein in its entirety for all purposes.

In some embodiments, the MDNA55 is diluted in artificial CSF. In some embodiments, the MDNA55 is diluted in an artificial cerebral spinal fluid (artificial CSF). In some embodiments, the artificial CSF comprises calcium chloride, dextrose, magnesium sulfate, potassium chloride, sodium bicarbonate, sodium chloride, sodium phosphate, dibasic, and is diluted in water. In some embodiments, the artificial CSF is Elliotts B® solution. In some embodiments, the artificial CSF is employed to produce an infusate having a final composition of MDNA55 at 3 μg/mL. In some embodiments, the artificial CSF is employed to produce an infusate having a final composition of MDNA55 at 3 μg/mL. In some embodiments, the artificial CSF is employed to produce an infusate having a final composition of MDNA55 at 3 μg/mL, 0.02% human serum albumin and optionally gadolinium-diethylenetriamine pentaacetic acid (Gd-DTPA, Magnevist®) at 7 mM.

In some embodiments, the formulation and routes of administration described herein allow for about 80%, about 85%, about 90%, about 95%, or about 100% of the tumor and the 1 cm margin around it (at risk for tumor spread) to be successfully covered. In some embodiments, the formulation and routes of administration described herein allow for about 80% to about 100% of the tumor and the 1 cm margin around it (at risk for tumor spread) to be successfully covered. In some embodiments, the formulation and routes of administration described herein allow for about 85% to about 100% of the tumor and the 1 cm margin around it (at risk for tumor spread) to be successfully covered. In some embodiments, the formulation and routes of administration described herein allow for about 90% to about 100% of the tumor and the 1 cm margin around it (at risk for tumor spread) to be successfully covered. In some embodiments, the formulation and routes of administration described herein allow for about 95% to about 100% of the tumor and the 1 cm margin around it (at risk for tumor spread) to be successfully covered. In some embodiments, the formulation and routes of administration described herein allow for about 100% of the tumor and the 1 cm margin around it (at risk for tumor spread) to be successfully covered.

TABLE 2

Reagents used in the Preparation of Infusate

| Reagent | Type | Grade | Manufacturer/Distributor |
|---|---|---|---|
| MDNA55 | Drug Product | CGMP, sterile | Medicenna Therapeutics Inc. |
| Artificial CSF e.g. Elliotts B ® Solution | Excipient | USP, sterile | Lukare Medical, LLC |
| HSA 5% (aqueous) Solution | Excipient | USP, sterile | Octapharma |
| Gd-DTPA, Magnevist ® 469.1 mg/mL (Optional) | Excipient | USP, sterile | Bayer Healthcare Pharmaceuticals Inc. |

Abbreviations: CGMP, Current Good Manufacturing Practice; NDC, National Drug Code; USP, United States Pharmacopeia A. Vascular Endothelial Growth Factor A (VEGF-A) Inhibitor—Including Avastin According to the present invention, MDNA55 can be administered in combination with sub therapeutically effective amounts of a VEGF-A inhibitor. In some embodiments, the VEGF-A inhibitor is Avastin. In some embodiments, the VEGF-A inhibitor is a biosimilar of Avasin, including but not limited to bevacizumab-awwb (Mvasi), bevacizumab-bvzr (Zirabev), Aybintio (also known as SB8), MYL-14020 (Abevmy), FKB238 (AstraZeneca/Fujifilm Kyowa Kirin Biologics), BCD-021 (Biocad, Russia), BCD500 (BIOCND, South Korea), Krabeva (Biocon, India), BAT1706 (Bio-Thera Solutions, China), BI 695502 (Boehringer Ingelheim), CT-P16 (Celltrion, South Korea), CHS-5217 (Coherus, USA), DRZ_BZ (Dr Reddy's Laboratories, India), Lumiere (Laboratorio Elea, Argentina), Cizumab (Hetero, India), IBI-305 (Innovent Biologics, China), MIL60 (Mabworks, China), Bevax (BEVZ92) (mAbxience, Spain), ONS-1045 (Oncobiologics/Viropro, USA), HD204 (Prestige Bio-pharma, Singapore), Bevacirel (Reliance Life Sciences/Lupin, India), HLX04 (Shanghai Henlius Biotech (Fosun Pharma, China), and TX16 (Tanvex BioPharma, Taiwan). In some embodiments, the VEGF-A inhibitor is bevacizumab-awwb (Mvasi). In some embodiments, the VEGF-A inhibitor is bevacizumab-bvzr (Zirabev). In some embodiments, the VEGF-A inhibitor is Aybintio (also known as SB8). In some embodiments, the VEGF-A inhibitor is MYL-14020 (Abevmy). In some embodiments, the VEGF-A inhibitor is FKB238. In some embodiments, the VEGF-A inhibitor is BCD-021 (Biocad, Russia). In some embodiments, the VEGF-A inhibitor is BCD500. In some embodiments, the VEGF-A inhibitor is Krabeva. In some embodiments, the VEGF-A inhibitor is BAT1706 ( ). In some embodiments, the VEGF-A inhibitor is BI 695502 (Boehringer Ingelheim). In some embodiments, the VEGF-A inhibitor is CT-P16. In some embodiments, the VEGF-A inhibitor is CHS-5217. In some embodiments, the VEGF-A inhibitor is DRZ_BZ. In some embodiments, the VEGF-A inhibitor is Lumiere. In some embodiments, the VEGF-A inhibitor is Cizumab (Hetero, India), IBI-305. In some embodiments, the VEGF-A inhibitor is MIL60. In some embodiments, the VEGF-A inhibitor is Bevax (BEVZ92). In some embodiments, the VEGF-A inhibitor is ONS-1045. In some embodiments, the VEGF-A inhibitor is HD204. In some embodiments, the VEGF-A inhibitor is Bevacirel. In some embodiments, the VEGF-A inhibitor is HLX04 (Shanghai Henlius Biotech. In some embodiments, the VEGF-A inhibitor is TX16.

The VEGF-A inhibitor can be administered before, during or after treatment with the anti-cancer therapeutic.

The terms "subtherapeutic effective amounts" or "sub therapeutically effective amounts" or "subtherapeutic dose" or "sub therapeutic dosage" refers to a dose or dosage or amount of a VEGF-A inhibitor that is below what is normally used for effectively treating a disease or producing an optimal therapeutic effect for a given VEGF-A inhibitor. For example, the approved dose of Avastin (bevacizumab) for treating recurrent glioblastoma is 10 mg/kg every 2 weeks. As a further example, the approved dosage of ZIRABEV (bevacizumab-bvzr; an Avastin biosimilar) is 10 mg/kg every 2 weeks. A subtherapeutic effective amounts of bevacizumab or a bevacizumab biosimilar used in combination with MDNA55 for treating recurrent glioblastoma can be any dose or dosage or amount below 10 mg/kg. In some embodiments, a subtherapeutic effective amounts of bevacizumab or a bevacizumab biosimilar used in combination with MDNA55 for treating recurrent glioblastoma can be any dose or dosage or amount below 7.5 mg/kg every 2 or 3 weeks, for example from 1 mg/kg to 7.5 mg/kg including 1, 1.5, 2, 2.5, 3, 3.5, 4, 4.5, 5, 5.5, 6, 6.5, 7, and 7.5 mg/kg every 2 weeks; or for example from 1 mg/kg to 7.5 mg/kg including 1, 1.5, 2, 2.5, 3, 3.5, 4, 4.5, 5, 5.5, 6, 6.5, 7, and 7.5 mg/kg every 3 weeks. In some embodiments, 5 mg/kg of bevacizumab or a bevacizumab biosimilar is used as an effective subtherapeutic amount every 2 weeks. In some embodiments, 7.5 mg/kg of bevacizumab or a bevacizumab biosimilar is used as an effective subtherapeutic amount every 3 weeks.

In some embodiments, MDNA55 is administered at least two weeks (e.g., 2, 3, 4, 5, 6, 7, 8, 9, 10, 11, 12, 13, 14, 15 weeks etc.) apart from the subtherapeutic dose of VEGF-A inhibitor (e.g., bevacizumab or a biosimilar of bevacizumab). In some embodiments, MDNA55 is administered at least three weeks (e.g., 3, 4, 5, 6, 7, 8, 9, 10, 11, 12, 13, 14, 15 weeks, etc.) apart from the subtherapeutic dose of VEGF-A inhibitor (e.g., bevacizumab or a biosimilar of bevacizumab). In some embodiments, MDNA55 is administered at least four weeks (e.g., 4, 5, 6, 7, 8, 9, 10, 11, 12, 13, 14, 15 weeks, etc.) apart from the subtherapeutic dose of VEGF-A inhibitor (e.g., bevacizumab or a biosimilar of bevacizumab).

In some embodiments, the VEGF-A inhibitor (e.g., bevacizumab or a biosimilar of bevacizumab) is administered at least two weeks apart from the MDNA55 and the VEGF-A inhibitor is administered at 5 mg/kg. In some embodiments, the VEGF-A inhibitor (e.g., bevacizumab or a biosimilar of bevacizumab) is administered at least three weeks apart from the MDNA55 and the VEGF-A inhibitor is administered at 7.5 mg/kg. In some embodiments, the MDNA55 administered is at a dose of about 240 μg. In some embodiments, the MDNA55 is administered is at a dose of below 240 μg.

In some embodiments, the VEGF-A inhibitor is administered at least two weeks (e.g., 2, 3, 4, 5, 6, 7, 8, 9, 10, 11, 12, 13, 14, 15 weeks etc.) apart from the MDNA55 for a period of at least 12 weeks, 16 weeks, 20 weeks, 24 weeks, 30 weeks, 36 weeks, 40 weeks, 44 weeks, 48 weeks, or 52 weeks or more. In some embodiments, the VEGF-A inhibitor is administered at least three weeks (e.g., 3, 4, 5, 6, 7, 8, 9, 10, 11, 12, 13, 14, 15 weeks etc.) apart from the MDNA55 for a period of at least 12 weeks, 16 weeks, 20 weeks, 24 weeks, 30 weeks, 36 weeks, 40 weeks, 44 weeks, 48 weeks, or 52 weeks or more. In some embodiments, the VEGF-A inhibitor is administered at least four weeks (e.g., 4, 5, 6, 7, 8, 9, 10, 11, 12, 13, 14, 15 weeks etc.) apart from the MDNA55 for a period of at least 12 weeks, 16 weeks, 20 weeks, 24 weeks, 30 weeks, 36 weeks, 40 weeks, 44 weeks, 48 weeks, or 52 weeks or more.

In some embodiments, the VEGF-A inhibitor is administered before the MDNA55. In some embodiments, the VEGF-A inhibitor is administered after the MDNA55.

B. MDNA55 Formulation Embodiment

MDNA55 Comprises SEQ ID NO:1:

```
MDTTEKETFCRAATVLRQFYSHHEKDTRCLGATAQQFHRH
KQLIRFLKLRDRNLWGLAGLNSCPVKEANQSTLENFLERL
KTIMREKYSKCSSGGNGGHKCDITLQEIIKTLNSLTEQKT
LCTELTVTDIFAASKASGGPEGGSLAALTAHQACHLPLET
FTRHRQPRGWEQLEQCGYPVQRLVALYLAARLSWNQVDQV
IRNALASPGSGGDLGEAIREQPEQARLALTLAAAESERFV
RQGTGNDEAGAANGPADSGDALLERNYPTGAEFLGDGGDV
SESTRGTQNWTVERLLQAHRQLEERGYVFVGYHGTFLEAA
QSIVEGGVRARSQDLDAIWRGFYIAGDPALAYGYAQDQEP
DARGRIRNGALLRVYVPRSSLPGFYRTSLTLAAPEAAGEV
ERLIGHPLPLRLDAITGPEEEGGRLETILGWPLAERTVVI
PSAIPTDPRNVGGDLDPSSIPDKEQAISALPDYASQPGKP
PKDEL
```

Composition of MDNA55: Drug product is supplied as a sterile frozen solution of MDNA55 at a concentration of 500 μg/mL contained in 0.5 mL Phosphate Buffered Saline (10 mM sodium phosphate, 500 mM sodium chloride, pH 7.4±0.1), filled in a sterile, single-use, 2 mL Type 1 USP dehydrogenated clear glass vial sealed with 13 mm Teflon-faced stopper and labeled.

MDNA55 Vial: MDNA55 contains 0.5 mL of MDNA55 (500 μg/m) and should be stored at ≤−70° C. The vial is labeled with "Sterile Single Dose Vials for Intratumoral Administration via Stereotactically Placed Catheters".

Storage: Drug product is stored at −70° C.+/−10° C. in its secondary packaging until required for preparation of infusate. Hospital pharmacy temperature monitoring records must be provided for all periods in which drug product vial(s) are stored for review by the study monitor.

Handling: Infusate will be prepared, using aseptic technique using a pre-sanitized biological safety (vertical flow) cabinet. After the preparation of the infusate, the used drug product vial should be discarded according to the hospital pharmacy's standard operating procedure.

Excipients

Upon receipt of shipment, the shipping container will be opened by the hospital pharmacist who must inspect condition of the contents and ensure that the excipient kits are undamaged. The pharmacist must follow the instructions that will be included in the shipment for downloading the TempTale monitor data as well as complete/return the proof of receipt documentation that arrives with the shipment whereby condition of receipt will be documented and recorded.

In some embodiments, MDNA55 is provided as part of a kit. In some embodiments, the MDNA55 is provided as a kit. In some embodiments, the kit contains 4 components:

Human Serum Albumin (HSA)

Artificial CSF e.g. Elliotts B Solution

Optional—Imaging tracer e.g. Magnevist (Gd-DTPA)

Empty IV Bag

The container has a tamper seal at the opening end to secure closure. One Excipient Kit is to be used for one infusate preparation.

Excipient Kit Components:

1×250 mL bottle HSA 5% (aqueous) Solution

1× unit Elliotts B Solution (10×10 mL ampules)

1×5 mL vial of Gd-DTPA

1× empty (150 mL size) IV Bag

The excipient kit components are to be used in MDNA55 infusate preparation as described in the present example. The kit provides materials for single (1×) MDNA55 infusate preparation.

Storage: Excipient kit is stored at controlled room temperature until required for preparation of infusate.

Handling: Excipient kit should be handled with care and stored right side up (label of kit in at the top).

Human Serum Albumin

In some embodiments, Human Serum Albumin (HSA) is added to the infusate, at a final concentration of 0.02%, to prevent adsorption of MDNA55 to the inner surfaces of the syringes, tubes and catheter used in the infusion assembly.

Supply: 1×250 mL bottle (Octapharma HSA 5% (aqueous) Solution, NCT #68982-0623-02)

Storage: at controlled room temperature as recommended by the manufacturer.

Handling: HSA should be handled using aseptic techniques in a pre-sanitized biological safety cabinet. Once opened and or used, the remaining HSA should be discarded according to the hospital pharmacy's standard operating procedure.

In some embodiments, the MDNA55 is buffered in an artificial CSF. In some embodiments, the artificial CSF is a buffered intrathecal electrolyte/dextrose injection (Elliotts B® Solution). In some embodiments, the MDNA55 drug product is diluted in Elliotts B® Solution.

In some embodiments, the MDNA55 is formulated with the ingredients listed in Table 3.

TABLE 3

| Composition/Information on Ingredients: | | | |
|---|---|---|---|
| Specific Chemical Identity | CAS # | Chemical Formula | Quantity per mL |
| Calcium Chloride | 10035-04-8 | $CaC1_2$ | 0.2 mg |
| Dextrose | 50-99-7 | $C_6H_{12}O_6$ | 0.8 mg |

TABLE 3-continued

| Composition/Information on Ingredients: | | | |
|---|---|---|---|
| Specific Chemical Identity | CAS # | Chemical Formula | Quantity per mL |
| Magnesium Sulfate | 10034-99-8 | $MgSO_4$ 7 $H_2O$ | 0.3 mg |
| Potassium Chloride | 7447-40-7 | KCl | 0.3 mg |
| Sodium Bicarbonate | 144-55-8 | $NaHCO_3$ | 1.9 mg |
| Sodium Chloride | 7647-14-5 | NaCl | 7.3 mg |
| Sodium Phosphate, Dibasic | 7782-85-6 | $Na_2HPO_4$ 7$H_2O$ | 0.2 mg |
| Water for Injection | 7732-18-5 | $H_2O$ | 1 mL |

Further information on the Elliott's B Solution. Elliotts B® Solution is a sterile, nonpyrogenic, isotonic solution containing no bacteriostatic preservatives.

Elliotts B Solution is a diluent for intrathecal administration of methotrexate sodium and cytarabine. Each 10 mL of Elliotts B Solution contains:

TABLE 4

| Composition per 10 mL of Elliotts B Solution | |
|---|---|
| Specific Chemical Identity | Quantity per 10 mL |
| Sodium Chloride, USP | 73 mg |
| Sodium Bicarbonate, USP | 19 mg |
| Dextrose, USP | 8 mg |
| Magnesium Sulfate•7H2O, USP | 3 mg |
| Potassium Chloride, USP | 3 mg |
| Calcium Chloride•2H2O, USP | 2 mg |
| Sodium Phosphate, dibasic•7H2O, USP | 2 mg |
| Water for Injection, USP qs 10 mL | To 10 mL |

TABLE 5

| Concentration of Electrolytes: | | | |
|---|---|---|---|
| Sodium | 149 mEq/liter | Bicarbonate | 22.6 mEq/liter |
| Potassium | 4.0 mEq/liter | Chloride | 132 mEq/liter |
| Calcium | 2.7 mEq/liter | Sulfate | 2.4 mEq/liter |
| Magnesium | 2.4 mEq/liter | Phosphate | 1.5 mEq/liter |

TABLE 6

| Formulae and molecular weights of the ingredients: | | |
|---|---|---|
| INGREDIENT | MOLECULAR FORMULA | MOLECULAR WEIGHT |
| Sodium Chloride | NaCl | 58.44 |
| Sodium Bicarbonate | NaHCO3 | 84.01 |
| Dextrose | C6H12O6 | 180.16 |
| Magnesium Sulfate•7H2O | Mg2SO4•7H2O | 246.48 |
| Potassium Chloride | KCl | 74.55 |

TABLE 6-continued

| Formulae and molecular weights of the ingredients: | | |
|---|---|---|
| INGREDIENT | MOLECULAR FORMULA | MOLECULAR WEIGHT |
| Calcium Chloride•2H2O | CaCl2•2H2O | 147.01 |
| Sodium Phosphate, dibasic•7H2O | Na2HPO4•7H2O | 268.07 |

The pH of Elliotts B Solution is 6.0-7.5, and the osmolarity is 288 mOsmol per liter (calculated).

Elliotts B Solution provides a buffered salt solution for use as a diluent for the intrathecal administration of methotrexate sodium and cytarabine. It has been demonstrated that Elliotts B Solution is comparable to cerebrospinal fluid in pH, electrolyte composition, glucose content, and osmolarity:

TABLE 7

| Comparison of Electrolyte Composition, pH and Nonelectrolytic Constituents of Elliotts B Solution and CSF: | | | | | | | | | |
|---|---|---|---|---|---|---|---|---|---|
| Solution | Na+ mEq/L | K+ mEq/L | Co++ mEq/L | Mg++ mEq/L | HCO3− mEq7L | Cl− mEq/L | pH | Phosphorus mg/dL | Glucose mg/dL |
| Cerebrospinal Fluid | 117-137 | 2.3-4.6 | 2.2 | 2.2 | 22.9 | 113-127 | 7.31 | 1.2-2.1 | 45-80 |
| Elliotts B Solution | 149 | 4.0 | 2.7 | 2.4 | 22.6 | 132 | 6.0-7.5 | 2.3 | 80 |

The approximate buffer capacity of Elliotts B Solution is $1.1\times10^{-2}$ equivalents when the challenge solution is 0.01N HCl and $7.8\times10^{-3}$ equivalents when the challenge solution is 0.01N NaOH. Compatibility studies with methotrexate sodium and cytarabine indicate these drugs are physically compatible with Elliotts B Solution.

Elliott's B solution is a diluent used in the preparation of infusate; it is comparable to cerebrospinal fluid in pH, electrolyte composition, glucose content, osmolarity and buffering capacity.

In some embodiments, the formulation optionally comprises gadolinium-diethylenetriamine pentaacetic acid (Gd-DTPA) Magnevist®. In some embodiments, when present, Gd-DTPA (diluted to ~1:70) is added to the infusate as a contrast agent as co-infusion of this surrogate tracer during infusion allows real-time monitoring of MDNA55 infusate distribution. When optionally used: supply: 1×5 mL single use vial of Gd-DTPA (Bayer HealthCare Pharmaceuticals Inc. Magnevist®; 469.1 mg/mL, NDC #50419-188-05) and store according to the manufacturer's instructions. Gd-DTPA (Magnevist®) should be handled using aseptic techniques in a pre-sanitized biological safety cabinet. Once opened or used, the remaining should be discarded in accordance with regulations dealing with the disposal of such materials and according to the hospital pharmacy's standard operating procedure.

C. Administration and Dosing

The MDNA55 can be used to treat, stabilize or prevent CNS cancer. MDNA55 can also be used in the treatment of indolent cancers, recurrent cancers including locally recurrent, distantly recurrent and/or refractory cancers (i.e. cancers that have not responded to other anti-cancer treatments), metastatic cancers, locally advanced cancers and aggressive cancers. In these contexts, the MDNA55 may exert either a cytotoxic or cytostatic effect resulting in, for example, a reduction in the number or growth of cancer cells and/or cancer stem cells, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptoms associated with a tumor, or an increase in the overall survival time of a subject having cancer.

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is begun soon after primary therapy, for example 2, 3, 4, 5, or 6 weeks after the last primary therapy treatment to delay recurrence, prolong survival or cure a subject. As noted above, it is contemplated that the MDNA55 can be used alone or in combination with one or more other chemotherapeutic agents as part of an adjuvant therapy. Combinations of the MDNA55 and standard chemotherapeutics may act to improve the efficacy of the chemotherapeutic and, therefore, can be used to improve standard cancer therapies. This application can be particularly important in the treatment of drug-resistant cancers which are not responsive to standard treatment. The dosage to be administered is not subject to defined limits, but it will usually be an effective amount. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The unit dosage forms may be administered once or multiple unit dosages may be administered, for example, throughout an organ, or solid tumor. Examples of ranges for the MDNA55 in each dosage unit are from about 0.0005 to about 100 mg, or more usually, from about 1.0 to about 1000 mg. Daily dosages of the MDNA55 typically are at least 1 ng/kg of body weight, at least 1 μg/kg of body weight, at least 1 mg/kg of body weight, for example fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances, dosage levels below the lower limit of the aforesaid range may be more than adequate, while in other cases still larger doses may be employed without causing harmful side effects, for example, by first dividing the larger dose into several smaller doses for administration throughout the day.

The MDNA55 can be used to treat and/or manage cancer, the methods include administering to a subject in need thereof a prophylactically or therapeutically effective regimen, the regimen comprising administering one or more therapies to the subject, wherein the regimen results in the stabilization or reduction in the cancer stem cell population and does not result in a reduction or only results in a small reduction of the circulating endothelial cell population and/or the circulating endothelial progenitor population. In one example, the regimen achieves a 5%-40%, a 10%-60%, or a 20 to 99% reduction in the cancer stem cell population and/or less than a 25%, less than a 15%, or less than a 10% reduction in the circulating endothelial cell population. In another example, the regimen achieves a 5%-40%, a 10%-60%, or a 20 to 99% reduction in the cancer stem cell population and/or less than a 25%, less than a 15%, or less than a 10% reduction in the circulating endothelial progenitor population. In another example, the regimen achieves a 5%-40%, a 10%-60%, or a 20 to 99% reduction in the cancer stem cell population and/or less than a 25%, less than a 15%, or less than a 10% reduction in the circulating endothelial cell population and the circulating endothelial progenitor population. In a specific example, the stabilization or reduction in the cancer stem cell population is achieved after two weeks, a month, two months, three months, four months, six month, nine months, 1 year, 2 years, 3 years, 4 years or more of administration of one or more of the therapies. In a particular example, the stabilization or reduction in the cancer stem cell population can be determined using any method known in the art. In certain examples, in accordance with the regimen, the circulating cancer stem cell population, the circulating endothelial cell population and/or the circulating endothelial progenitor population is monitored periodically (e.g., after 2, 5, 10, 20, 30 or more doses of one or more of the therapies or after 2 weeks, 1 month, 2 months, 6 months, 1 year, or more of receiving one or more therapies).

In some embodiments, a single infusion of MDNA55 is administered at a concentration of 1.5 μg/mL (and up to 8 μg/mL). In some embodiments, a single infusion of MDNA55 is administered at a concentration of about 6 μg/mL. In some embodiments, infusion volume and parameters can be personalized for each subject/patient to achieve target coverage to the maximum extent possible. In some embodiments, infused volume will range from approximately 7 mL (smallest tumor) to 60 mL (largest tumor). In some embodiments, the duration of infusion will be approximately 6 to 32 hours depending on tumor volume, flow rate and number of catheters. In some embodiments, the maximum delivered dose will be 240 μg, including 240 μg, 230 μg, 220 μg, 210 μg, 200 μg, 190 μg, 180 μg, 170 μg, 160 μg, 150 μg, 140 μg, 130 μg, 120 μg, 110 μg, 100 μg, 90 μg, 80 μg, 70 μg, 60 μg, 50 μg, 40 μg, 30 μg, 20 μg, and 10 μg. In some embodiments, the dosage is administered intra-cranially. In some embodiments, MDNA55 is administered as a single dose of about 90 μg (e.g., 1.5 μg/mL in 60 mL), about 180 (e.g., 3 μg/mL in 60 mL or 4.5 μg/mL in 40 mL), or about 240 μg (e.g., 6 μg/mL in 40 mL, or 4 μg/mL in 60 mL). In some embodiments, MDNA55 is administered as a single dose of about 1.5 μg/mL to about 8 μg/mL. In some embodiments, MDNA55 is administered as a single dose of about 4 μg/mL or about 6 μg/mL.

In some embodiments, the dosing is 240 μg, or 6 μg/mL× 40 mL, of MDNA55 per subject. In some embodiments, the dosing is from about 1.5 μg/mL to about 8.0 μg/mL. In some embodiments, the dosing is about 1.5 μg/m, 2 μg/mL, 2.5 μg/mL, 3.0 μg/mL, 3.5 μg/mL, 4 μg/mL, 4.5 μg/mL, 5 μg/mL, 5.5 μg/mL, 6 μg/mL, 6.5 μg/mL, 7 μg/mL, 7.5 μg/mL or 8 μg/mL. In some embodiments, the dosage is for MDNA55.

In some embodiments, the dosing flow rate is about 1 μL/min/catheter to about 20 μL/min/catheter. In some embodiments, the dosing flow rate is about 3 μL/min/catheter to about 10 μL/min/catheter. In some embodiments, the dosing flow rate is about 15 μL/min/catheter. In some embodiments, the dosing flow rate is about 1 μL/min/catheter to about 20 μL/min/catheter. In some embodiments, the dosing flow rate is about 3 μL/min/catheter to about 10 μL/min/catheter. In some embodiments, 1-4 catheters are employed. In some embodiments, 1-3 catheters are employed. In some embodiments, 1-3 catheters are employed and the flow-rates of up to 15 μL/min/catheter. In some embodiments, 1.5 μg/mL is administered via 1-3 catheters and the flow-rates of up to 15 μL/min/catheter. In some embodiments, 1.5 μg/mL is administered via 1-3 catheters and the flow-rates of up to 15 μL/min/catheter with a total dosage of 90 μg of MDNA55. In some embodiments, 3 μg/mL is administered via 1-3 catheters and the flow-rates of up to 10 μL/min/catheter. In some embodiments, 1.5 μg/mL is administered via 1-3 catheters and the flow-rates of up to 15 μL/min/catheter with a total dosage of 240 μg of MDNA55.

D. Treatment of Glioblastoma

In some embodiments, MDNA55 is employed for the treatment of a brain tumor. In some embodiments, the brain tumors is glioblastoma (GB). Glioblastoma (GB) is an aggressive brain tumor characterized by rapid proliferation of undifferentiated cells, extensive infiltration, and a high propensity to recur (Hamstra et al., 2005). It is a rapidly progressing and universally fatal cancer. For adults treated with concurrent Temozolomide (Termodar®) and radiotherapy, median survival is 14.6 months, two-year survival is approximately 30%, and five-year survival approximately 10%. Clinical impact is defined by rapid neurologic deterioration which affects the ability to perform everyday functions, such as eating, walking, and talking. There can also be distortion of personality and identity, such as mood, memory, emotion, and intelligence. GB does not typically metastasize outside of the CNS and death usually results due to increased intracranial pressure and herniation caused by uncontrolled growth of tumor within the bone-encased brain cavity. Annual worldwide incidence of primary GB in well-resourced countries is approximately 27,500 (Decision Recourses, 2013).

In some embodiments, MDNA55 is employed for the treatment of a brain tumor over-expressing IL-4R, for example, mixed adult glioma, mixed pediatric glioma, diffuse intrinsic pontine gliomas (DIPG), medulloblastoma, adult pituitary adenoma, meningioma.

E. Biomarkers and Patient Populations

MDNA55 finds use for the treatment of GB including recurrent GB, brain metastasis, newly diagnosed GB, and diffuse intrinsic pontine glioma in particular patient populations.

In some embodiments, the cancer biopsy and autopsy samples are from adult and pediatric CNS tumors (e.g., brain tumors). In some embodiments, the patient has glioblastoma (also called glioblastoma multiform—GBM). In some embodiments, the patient has recurrent GB. In some embodiments, the patient has brain metastasis from GB. In some embodiments, the patient has newly diagnosed GB. In some embodiments, the patient has diffuse intrinsic pontine glioma. In some embodiments, the patient tumor samples have been shown to over-express the IL-4R as compared to little or no IL-4R expression in normal adult and pediatric brain tissue (Puri et al., 1994a; Kawakami et al., 2002a; Joshi, et al., 2001; Konanbash et al., 2013). While not being bound by theory, cells that do not express the IL-4R target do not bind to MDNA55 and are, therefore, not subject to PE-mediated effects (Kawakami et al., 2002).

In some embodiments, MDNA55 induces tumor growth killing that is not growth-rate dependent (Li and Hall, 2010). In some embodiments, quiescent cancer cells and/or cancer stem cells and slower growing non-malignant cells of the tumor microenvironment (TME) may be as sensitive to MDNA55 as rapidly dividing tumor cells.

In some embodiments, the cancer cells are $O^6$-methylguanine-methyltransferase (MGMT) positive. In some embodiments, the cancer cells are $O^6$-methylguanine-methyltransferase (MGMT) negative. In some embodiments, the cancer cells have methylated MGMT gene promoter. In some embodiments, the cancer cells have unmethylated MGMT gene promoter. In some embodiments, $O^6$-methylguanine-methyltransferase (MGMT) positive cancer cells (harboring unmethylated MGMT promoters and therefore resistant to Temozolomide) are sensitive to MDNA55. Exemplary sensitive CNS cancer cell lines include T98G (glioblastoma) and have been shown to over-express MGMT. Such cell lines are resistant to alkylating agents such as Temozolomide (Huang et al., 2012; Kuo et al., 2007; Kokkinakis et al., 2003), but can be sensitive to MDNA55. In some embodiments, cancer cells harboring methylated MGMT gene promoter are sensitive to MDNA55.

In some embodiments, IL-4R-expressing cell lines show picomolar sensitivity to MDNA55. See, for example, Puri et al., 1996b; Kreitman et al., 1995; Shimamura et al., 2007. In some embodiments, MGMT expressing tumors exhibit sensitivity to MDNA55 of the present invention. In some embodiments, IL-4R-expressing tumors exhibit picomolar sensitivity to MDNA55 of the present invention. In some embodiments, IL-4R-expressing glioblastomas exhibit sensitivity to MDNA55. In some embodiments, MGMT-expressing tumors exhibit sensitivity to MDNA55. In some embodiments, MGMT-expressing glioblastomas exhibit sensitivity to MDNA55.

Furin like protease cleavage of MDNA55 and result in activation of the PE toxin (Chironi et al., 1997; Shapira and Benhar, 2010) and glioblastomas often express furin (Mercapide, et al., 2002; Wick et al., 2004). The higher expression levels of furin in glioma cells as opposed to normal cells provides additional tumor specificity and also a contributes to factor to the exceptional picomolar sensitivity of cancer cells to MDNA55. In some embodiments, the tumor expresses furin. In some embodiments, the tumor expressing furin is more sensitive to MDNA55 than normal non-tumor cells.

IL-4R is over-expressed not only by CNS tumors but also by non-malignant cells (MDSCs and TAMs) of the immunosuppressive TME. In some embodiments, MDNA55 finds use in the treatment adult and pediatric patients with aggressive forms of primary and metastatic brain cancer.

GB has a robust immunosuppressive TME and may comprise up to 40% of the tumor mass (Kennedy et al., 2013). Recently, it has been shown that malignant gliomas have a T-helper cell type-2 (Th2) bias and are heavily infiltrated by myeloid derived suppressor cells (MDSCs) and tumor associated macrophages (TAMs) and that the IL4/IL-4R bias mediates their immunosuppressive functions (Harshyne, et al., 2016). Furthermore, IL-4R is up-regulated on glioma-infiltrating myeloid cells but not in the periphery or in normal brain (Kohanbash et al., 2013). In some embodiments, purging Th2 cells, MDSCs, and TAMs using MDNA55 may alleviate the immune block associated with cancer. In some embodiments, the alleviation of immune block promotes anti-tumor immunity and aid in long-term disease control and/or disease treatment.

F. IL-4R as a Biomarker or Companion Diagnostic

In some embodiments, the level of IL-4R (also referred to as "IL4R") expression can be employed as a biomarker or companion diagnostic for use in the determining treatment regimens as well as predicting or determining treatment efficacy. In some embodiments, the level of Type 2 IL-4R (Type II IL-R4, comprising IL-4Rα and IL-13Rα1) expression can be employed as a biomarker or companion diagnostic for use in the determining treatment regimens as well as predicting or determining treatment efficacy. In some embodiments, IL-4Rα is reactive in the cytoplasm of tumor cells. However, IL-4Rα also be observed in serum and occasionally in the cytoplasm of normal cells and normal tissue components.

In some embodiments, the level of IL-4R expression is determined by measuring IL-4Rα expression. In some embodiments, the level of IL-4R expression, including the level of IL-4Rα expression, is scored by a board-certified pathologist. In some embodiments, the level of expression of Type 2 IL-4R (Type II IL-4R, comprising IL-4Rα and IL-13Rα1) is determined by measuring IL-4Rα expression. In some embodiments, the level of expression of Type 2 IL-4R (Type II IL-R4, comprising IL-4Rα and IL-13Rα1) is scored by a board-certified pathologist.

There are two main components to scoring malignant tumor cells, which include Percent Scores and an H-Scores (derived from percentages that are recorded at differential intensities) as described below. In some embodiments, any IL-4Rα staining observed in cells that are clearly non-neoplastic can be excluded. In some embodiments, malignant cells are considered to express IL-4Rα if cytoplasmic tumor cell staining is recognized.

Percent Score Method

Percent Scores are calculated by summing the percentages of intensities in tumor cells at either ≥1+, ≥2+ or ≥3+. Thus, scores range from 0 to 100.

Percent Score ≥1+=(% at 1+)+(% at 2+)+(% at 3+)

Percent Score ≥2+=(% at 2+)+(% at 3+)

Percent Score ≥3+=(% at 3+)

In some embodiments, a high level of IL-4R expression is indicated by a percent score of ≥2+. In some embodiments, a high level of IL-4R expression is indicated by a percent score of ≥3+.

In some embodiments, a moderate level of IL-4R expression is indicated by a percent score of ≥1+ but <2.

In some embodiments, no detectable level of IL-4R expression is indicated by a percent score of 0. In some embodiments, a low level of IL-4R expression is indicated by a percent score of ≥1+.

H-Score Method

The H-Score is calculated by summing the percentage of tumor cells with intensity of expression (brown staining) multiplied by their corresponding intensity a four-point semi-quantitative scale (0, 1+, 2+, 3+). Thus, scores range from 0 to 300.

H-Score=[(% at <1)×0]+[(% at 1+)×1]+[(% at 2+)×2]+[(% at 3+)×3]

For both the Percent Score and H-Score methods, the four-point semi-quantitative intensity scale is described as follows: 0—null, negative or non-specific staining, 1+—low or weak staining, 2+—medium or moderate staining, and 3+—high or strong staining. The percentage at each intensity is estimated directly and typically reported as one of the following, though other increments can also be used: 0, 1, 2, 3, 4, 5, 10, 15, 20, 25, 30, 35, 40, 45, 50, 55, 60, 65, 70, 75, 80, 85, 90, 95, 96, 97, 98, 99, or 100%.

In some embodiments, no level of IL-4R expression to a low level of IL-4R expression is indicated by H-Scores from 0 to 75 (e.g., no to low expression).

In some embodiments, a moderate level of IL-4R expression is indicated by H-Scores from 76 to 150 (e.g., moderate expression).

In some embodiments, a high level of IL-4R expression is indicated by H-Scores from 151 to 225 (e.g., high expression).

In some embodiments, a high level of IL-4R expression is indicated by H-Scores from 226 to 300 (e.g., very high expression).

In some embodiments, a moderate or high level of IL-4R expression is indicated by H-Scores >75. In some embodiments, a moderate or high level of IL-4R expression is indicated by H-Scores from 76 to 300. In some embodiments, a moderate or high level of IL-4R expression is indicated by H-Scores from 80 to 300. In some embodiments, a moderate or high level of IL-4R expression is indicated by H-Scores from 90 to 300. In some embodiments, a moderate or high level of IL-4R expression is indicated by H-Scores from 95 to 300. In some embodiments, a moderate or high level of IL-4R expression is indicated by H-Scores from 100 to 300. In some embodiments, a moderate or high level of IL-4R expression is indicated by H-Scores from 105 to 300. In some embodiments, a moderate or high level of IL-4R expression is indicated by H-Scores from 110 to 300. In some embodiments, a moderate or high level of IL-4R expression is indicated by H-Scores from 115 to 300. In some embodiments, a moderate or high level of IL-4R expression is indicated by H-Scores from 120 to 300. In some embodiments, a moderate or high level of IL-4R expression is indicated by H-Scores from 125 to 300. In some embodiments, a moderate or high level of IL-4R expression is indicated by H-Scores from 130 to 300. In some embodiments, a moderate or high level of IL-4R expression is indicated by H-Scores from 135 to 300. In some embodiments, a moderate or high level of IL-4R expression is indicated by H-Scores from 140 to 300. In some embodiments, a moderate or high level of IL-4R expression is indicated by H-Scores from 145 to 300. In some embodiments, a moderate or high level of IL-4R expression is indicated by H-Scores from 150 to 300. In some embodiments, a moderate or high level of IL-4R expression is indicated by H-Scores from 155 to 300. In some embodiments, a moderate or high level of IL-4R expression is indicated by H-Scores from 160 to 300. In some embodiments, a moderate or high level of IL-4R expression is indicated by H-Scores from 165 to 300. In some embodiments, a moderate or high level of IL-4R expression is indicated by H-Scores from 170 to 300. In some embodiments, a moderate or high level of IL-4R expression is indicated by H-Scores from 175 to 300. In some embodiments, a moderate or high level of IL-4R expression is indicated by H-Scores from 180 to 300. In some embodiments, a moderate or high level of IL-4R expression is indicated by H-Scores from 185 to 300. In some embodiments, a moderate or high level of IL-4R expression is indicated by H-Scores from 190 to 300. In some embodiments, a moderate or high level of IL-4R expression is indicated by H-Scores from 195 to 300. In some embodiments, a moderate or high level of IL-4R expression is indicated by H-Scores from 200 to 300. In some embodiments, a moderate or high level of IL-4R expression is indicated by H-Scores from 205 to 300. In some embodiments, a moderate or high level of IL-4R expression is indicated by H-Scores from 210 to 300. In some embodiments, a moderate or high level of IL-4R expression is indicated by H-Scores from 215 to 300. In some embodiments, a moderate or high level of IL-4R expression is indicated by H-Scores from 220 to 300. In some embodiments, a moderate or high level of IL-4R expression is indicated by H-Scores from 225 to 300. In some embodiments, a moderate or high level of IL-4R expression is indicated by H-Scores from 230 to 300. In some embodiments, a moderate or high level of IL-4R expression is indicated by H-Scores from 235 to 300. In some embodiments, a moderate or high level of IL-4R expression is indicated by H-Scores from 240 to 300. In some embodiments, a moderate or high level of IL-4R expression is indicated by H-Scores from 245 to 300. In some embodiments, a moderate or high level of IL-4R expression is indicated by H-Scores from 250 to 300. In some embodiments, a moderate or high level of IL-4R expression is indicated by H-Scores from 255 to 300. In some embodiments, a moderate or high level of IL-4R expression is indicated by H-Scores from 265 to 300. In some embodiments, a moderate or high level of IL-4R expression is indicated by H-Scores from 270 to 300. In some embodiments, a moderate or high level of IL-4R expression is indicated by H-Scores from 275 to 300. In some embodiments, a moderate or high level of IL-4R expression is indicated by H-Scores from 280 to 300. In some embodiments, a moderate or high level of IL-4R expression is indicated by H-Scores from 285 to 300. In some embodiments, a moderate or high level of IL-4R expression is indicated by H-Scores from 290 to 300. In some embodiments, a moderate or high level of IL-4R expression is indicated by H-Scores from 295 to 300.

Occasionally, cancer samples, including GB samples included background IL-4Rα staining throughout benign tissue. When present, such interstitial staining was captured with an average intensity score of 1+, 2+, or 3+ to record the level of background cytoplasmic staining present around tumor cells. When absent, this value was recorded as NA (not applicable). In some embodiments, high background reactivity could contribute to higher IL-4Rα expression in tumor cells. As such, in some embodiments, the interstitial staining score should be taken into consideration when evaluating reactivity scores for malignant tumor cells.

G. Kits

IL-4R expression can be detected using either IHC or RT-PCR analyses. In some embodiment, and RT-PCR based method and associated kit can be employed. In some embodiments, an IL-4R antibody based method for detection and associated kit can be employed. Antibodies to IL-4R that find use in such kits can include commercially available as well as other known or developed IL-4R antibodies. In some embodiments, an IL-4R antibody can be employed in an immunohistochemistry (IHC)-based assay for detecting IL-4R expression. In some embodiments, the IL-4R is a monoclonal antibody to the IL-4Rα chain, Joshi et al., (Joshi B H, et al., In situ expression of interleukin-4 (IL-4) receptors in human brain tumors and cytotoxicity of a recombinant IL-4 cytotoxin in primary glioblastoma cell cultures. Cancer Res. 2001; 61:8058-8061) evaluated expression in surgical/biopsy samples of brain tumor tissues by IHC. 83% (Ichinose, M., et al., Cancer Res. 2002, and Johnson H, et al., Mol. Cell Proteomics. 2012 December; 11(12):1724-40) of GB were moderately to intensely positive for IL-4Rα (Joshi B H, et al. In situ expression of interleukin-4 (IL-4) receptors in human brain tumors and cytotoxicity of a recombinant IL-4 cytotoxin in primary glioblastoma cell cultures. Cancer Res. 2001; 61:8058-8061), whereas 11 of 11 normal brain samples showed no detectable staining for IL-4R, demonstrating tumor specificity.

In some embodiments, the level of IL-4R can be employed as a companion diagnostic and/or predictive marker to select IL-4R positive patients for therapeutic treatment with MDNA55 of the present invention. In some embodiments, the level of Type 2 IL-4R (Type II IL-R4, comprising IL-4Rα and IL-13Rα1) can be employed as a companion diagnostic and/or predictive marker to select IL-4R positive patients for therapeutic treatment with MDNA55 of the present invention.

In some embodiments, the present invention provides a kit for detecting IL-4R expression. In some embodiments, the present invention provides a kit for detecting Type 2 IL-4R (Type II IL-R4, comprising IL-4Rα and IL-13Rα1) expression. In some embodiments, the kit provides the components for RT-PCR based detection of IL-4R mRNA expression levels. In some embodiments, the kit provides the components for an immunohistochemistry (IHC)-based assay for detecting or measuring IL-4R expression. In some embodiments, the kit comprises an IL-4R antibody and instructions for using the IL-4R antibody in an immunohistochemistry (IHC)-based assay. In some embodiments, the kit further comprises instructions for determining the percent score. In some embodiments, the kit further comprises instructions for determining the H-Score. In some embodiments, the kit comprises an IL-4R antibody, instructions for using the IL-4R antibody in an immunohistochemistry (IHC)-based assay, and instructions for determining the percent score. In some embodiments, the kit comprises an IL-4R antibody, instructions for using the IL-4R antibody in an immunohistochemistry (IHC)-based assay, and instructions for determining the H-Score. In some embodiments, the kit comprises an IL-4Rα antibody, instructions for using the IL-4Rα antibody in an immunohistochemistry (IHC)-based assay, and instructions for determining the percent score. In some embodiments, the kit comprises an IL-4Rα antibody, instructions for using the IL-4Rα antibody in an immunohistochemistry (IHC)-based assay, and instructions for determining the H-Score.

H. Convection Enhanced Delivery (CED)

The present invention contemplates the use of CED for delivery of therapeutics directly into the tumor. CED has been described in Patel et al., Neurosurgery 56: 1243-52, 2005, (incorporated by reference herein in its entirety). This enables high local drug concentrations to be achieved while limiting systemic toxicity. The procedure has been used in the treatment of recurrent GB and other CNS disorders from early clinical development through to Phase 3 clinical trials with a good safety profile. In some embodiments, MDNA55 is delivered by convection-enhanced delivery (CED) intratumorally. In some embodiments, CED is performed by direct infusion through intracranial catheters (1 or more, depending on the size of the tumor) under constant pressure.

In some embodiments, this is over a period of 1 to 7 days. The total dose of MDNA55 is about 90-100 μg. In some embodiments, the dosage can be adjusted within the range of range 5 μg to 1 mg. In some embodiments, MRI imaging prior to, during and following infusion is used to monitor drug distribution and tumor response. In some embodiments, subjects/patients are monitored by clinical evaluation and MRI on an ongoing basis after treatment.

In some embodiments, CED will be employed to administer MDNA55 to the CNS tumor. In some embodiments, CED will be employed to administer MDNA55 for the treatment of CNS tumors. In some embodiments, CED will be employed to administer MDNA55 for the treatment of GB. In some embodiments, CED will be employed to administer MDNA55 for the treatment of progressive and/or recurrent GB.

In some embodiments, the CED process will employ the use of planning high precision planning software (e.g. iPlan® Flow Infusion Version 3.0.6, Brainlab AG) for determining catheter placement. In some embodiments, the CED process will employ catheters specifically designed for brain usage. In some embodiments, the CED process will not employ large diameter ventricular catheters, which can be prone to drug leakage from the intended delivery site.

In some embodiments, the CED process will include co-infusion of an optional surrogate tracer, for example, a magnetic resonance imaging (MRI) contrast agent, will allow real-time monitoring of MDNA55 distribution ensuring adequate coverage of the tumor and the infiltrative edges.

In some embodiments, the optional surrogate tracer molecule can include but is no limited to any magnetic resonance imaging tracer. In some embodiments, the surrogate tracer is a gadolinium bound tracer. In some embodiments, the optional surrogate tracer is selected from the group consisting of gadolinium-diethylenetriamine pentaacetic acid [Magnevist®] [Gd-DTPA]; commercially available from Bayer Healthcare Pharmaceuticals, Inc.) and gadolinium-bound albumin (Gd-albumin). In some embodiments, the optional surrogate tracer used during CED will enable effective real-time monitoring of drug distribution. In some embodiments, the real-time monitoring allows for ensuring adequate coverage of the tumor and the peritumoral infiltrating margin with the MDNA55. In some embodiments, the surrogate tracer can be administered in combination with MDNA55 to determine if the MDNA55 is delivered to a tumor, such as a brain tumor, safely at therapeutic doses while monitoring its distribution in real-time.

For further information regarding on CED and optional surrogate tracers, see for example, Chittiboina et al., 2014; Jahangiri et al., 2016; and Murad et al., Clin. Cancer Res. 12(10):3145-51, 2006), all of which are incorporated herein by reference in their entireties.

I. Monitoring Treatment

Any in vitro or in vivo (ex vivo) assays known to one of ordinary skill in the art that can detect and/or quantify cancer cells and/or cancer stem cells can be used to monitor cancer cells and/or cancer stem cells in order to evaluate the impact of a treatment utilizing a MDNA55. These methods can be used to assess the impact in a research setting as well as in a clinical setting. The results of these assays then may be used to alter the treatment of a subject. Assays for the identification of cancer cells and/or cancer stem cells are provided in US patent application no. 2007/0292389 to Stassi et al. (herein incorporated by reference).

Cancer cells and/or cancer stem cells usually are a subpopulation of tumor cells. Cancer cells and/or cancer stem cells can be found in biological samples derived from cell culture or from subjects (such as a tumor sample). Various compounds such as water, salts, glycerin, glucose, an antimicrobial agent, paraffin, a chemical stabilizing agent, heparin, an anticoagulant, or a buffering agent can be added to the sample. The sample can include blood, serum, urine, bone marrow or interstitial fluid. In another example, the sample is a tissue sample. In a particular example, the tissue sample is breast, brain, skin, colon, lung, liver, ovarian, pancreatic, prostate, renal, bone or skin tissue. In a specific example, the tissue sample is a biopsy of normal or tumor tissue. The amount of biological sample taken from the subject will vary according to the type of biological sample and the method of detection to be employed. In a particular example, the biological sample is blood, serum, urine, or bone marrow and the amount of blood, serum, urine, or bone marrow taken from the subject is 0.1 mL, 0.5 mL, 1 mL, 5 mL, 8 mL, 10 mL or more. In another example, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

A test sample can be a sample derived from a subject that has been treated with MDNA55. Test samples can also include control samples. In some examples a control sample is from a subject prior to treatment with MDNA55, and in other examples the test sample can be taken from a different location within a subject that has been treated with MDNA55. Control samples can also be derived from cells that have been artificially cultured. The sample can be subjected to one or more pretreatment steps prior to the detection and/or measurement of the cancer stem cell population in the sample. In certain examples, a biological fluid is pretreated by centrifugation, filtration, precipitation, dialysis, or chromatography, or by a combination of such pretreatment steps. In other examples, a tissue sample is pretreated by freezing, chemical fixation, paraffin embedding, dehydration, permeabilization, or homogenization followed by centrifugation, filtration, precipitation, dialysis, or chromatography, or by a combination of such pretreatment steps. In certain examples, the sample is pretreated by removing cells other than stem cells or cancer cells and/or cancer stem cells from the sample, or removing debris from the sample prior to the determination of the amount of cancer cells and/or cancer stem cells in the sample.

In certain examples, the amount of cancer cells and/or cancer stem cells in a subject or a sample from a subject is/are assessed prior to therapy or regimen to establish a baseline. In other examples the sample is derived from a subject that was treated using MDNA55. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the amount of cancer cells and/or cancer stem cells is assessed after a certain number of doses (e.g., after 2, 5, 10, 20, 30 or more doses of a therapy). In other examples, the amount of cancer cells and/or cancer stem cells is assessed after 1 week, 2 weeks, 1 month, 2 months, 1 year, 2 years, 3 years, 4 years or more after receiving one or more therapies.

Targets on cancer cells and/or cancer stem cells are also expressed on normal noncancerous cells. Therefore, in some examples the identification of cancer cells and/or cancer stem cells can be made by comparing the relative amount of signal generated from target binding in a control sample and comparing it to the test sample for which the presence or absence of cancer cells and/or cancer stem cells is being determined. In such examples, the number, quantity, amount or relative amount of cancer cells and/or cancer stem cells in a sample can be expressed as the percentage of, e.g., overall cells, overall cancerous cells or overall stem cells in the sample.

The results from testing a sample for the presence of cancer cells and/or cancer stem cells and/or the amount of cancer cells and/or cancer stem cells present can be used to alter treatment regimes, including altering the MDNA55 treatment regimen. For example, if testing before and after treatment reveals that the population of cancer cells and/or cancer stem cells increased and/or did not decrease treatment can be altered.

The amount of cancer cells and/or cancer stem cells can be monitored/assessed using standard techniques known to one of ordinary skill in the art. Cancer cells and/or cancer stem cells can be monitored by obtaining a sample, and detecting cancer cells and/or cancer stem cells in the sample. The amount of cancer cells and/or cancer stem cells in a sample (which may be expressed as percentages of, e.g., overall cells or overall cancer cells) can be assessed by detecting the expression of antigens on cancer cells and/or cancer stem cells. Any technique known to those skilled in the art can be used for assessing the population of the cancer cells and/or cancer stem cells. Antigen expression can be assayed, for example, by immunoassays including, but not limited to, western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, protein A immunoassays, flow cytometry, and FACS analysis. In such circumstances, the amount of cancer cells and/or cancer stem cells in a test sample from a subject may be determined by comparing the results to the amount of stem cells in a reference sample (e.g., a sample from a subject who has no detectable cancer) or to a predetermined reference range, or to the patient him/herself at an earlier time point (e.g., prior to, or during therapy). For the purposes of immunoassays one or more of the targets displayed by the cancer stem cell can be used as the target for the immunoassay.

For example, brain cancer cells and/or cancer stem cells can be identified using a CD133+ target, as well as other targets known to be expressed on brain cancer cells and/or cancer stem cells. Additional exemplary markers can be found in Sakariassen et al., Neoplasia 9(11):882-92, 2007 and Vermeulen et al., Cell. Death Differ. 15(6):947-58, 2008 and U.S. patent application 2008/0118518, which is herein incorporated by reference.

In some embodiments, treatment can be monitoring using an IL-4R biomarker expression level, as described in the next section below.

In some embodiments, efficacy endpoints, such as progression-free survival (PFS), objective response rate (ORR), overall survival (OS), duration of response (DOR), and duration of clinical benefit (DOCB) are evaluated after the treatment. These efficacy endpoints can be correlated with the IL-4R biomarker expression level in subjects before and after the treatment. In some embodiments, there is an increase in progression-free survival (PFS). In some embodiments, there is an increase in objective response rate (ORR). In some embodiments, there is an increase in overall survival (OS). In some embodiments, there is an increase in duration of response (DOR). In some embodiments, there is an increase in duration of clinical benefit (DOCB) are evaluated after the treatment. In some embodiments, the efficacy endpoint is determined as a percentage increase over base line. In some embodiments, the increase is an increase of about 10%, 15%, 20%, 25%, 30%, 35%, 40%, 45%, 50%, 55%, 60%, 65%, 70%, 75%, 80%, 85%, 90%, 95%, or 100% or more over base line. In some embodiments, the increase is an increase of about 1-fold, 2-fold, 3-fold, 4-fold, and/or 5-fold.

EXAMPLES

Example I. Treatment Using MDNA55 in Combination with a VEGF-A Inhibitor

The effect MDNA55 in combination with an exemplary vascular endothelial growth factor A (VEGF-A) inhibitor (e.g., bevacizumab) was tested in adults with recurrent or progressive glioblastoma, a type of a central nervous system (CNS) tumor.

MDNA55 (SEQ ID NO: 1) is a fusion toxin comprising a genetically engineered circularly permuted interleukin-4 (cpIL-4) fused to a modified version of the *Pseudomonas aeruginosa* exotoxin A (PE). MDNA55 binds to the IL-4 receptor (IL4R), over-expressed by cancer cells and non-malignant immunosuppressive cells of the tumor microenvironment (TME), and delivers a potent cell-killing agent, PE. A large percentage of glioblastomas (GBs) and their TME express IL4R in relatively high amounts, making it a relevant target for MDNA55.

Convection enhanced delivery (CED) method was used to administer MDNA55 and bevacizumab or MDNA55 alone into the tumor site(s) in the patients via intra- and peritumoral infusion. The CED method minimizes systemic exposure to the fusion toxin, and the image-guided CED technique enhances exposure of active drug throughout the target region.

Patients selection criteria includes male and female subjects ≥18 years of age who had primary (de novo) GB that had recurred or progressed (per standard RANO criteria), with a life expectancy >12 weeks and a Karnofsky performance status (KPS)≥70. Subjects had to have tumor diameter of ≥1 cm×≥1 cm (minimum) to 4 cm in any direction by pre-interventional magnetic resonance imaging (MRI; within 14 days of planned treatment) and could not have features which made the tumor a poor target for CED (e.g., significant liquefaction or geometric features not conducive to CED).

MDNA55 formulated in Elliots solution or an artificial cerebral spinal fluid (CSF) solution containing albumin and a subtherapeutic dose of bevacizumab were administered separately via infusion using CED with precision planning and realtime MRI monitoring of infusate distribution. The infusion aimed to achieve coverage of the tumor and the peritumoral margin to the maximum extent possible as indicated by distribution of a co-infused gadolinium tracer observed by MRI. Pre-treatment catheter trajectory planning was performed with aim to place up to 4 catheters but a minimum of 2 catheters, depending upon the tumor size. Planning for catheter placement would only target the enhancing region of the tumor on MRI. Each subject received an individualized volume of MDNA55 and bevacizumab (according to tumor size). The amount of MDNA55 administered was 240 μg (e.g., 4.0 μg/mL in 60 ml or 6.0

μg/mL in 40 ml) and bevacizumab administered was 5 mg/kg-7.5 mg/kg. In some embodiments, the amount of MDNA55 administered was 240 μg (e.g., 4.0 μg/mL in 60 ml or 6.0 μg/mL in 40 ml) and bevacizumab administered was 5 mg/kg with two weeks between administration of the MDNA55 and the bevacizumab. In some embodiments, the amount of MDNA55 administered was 240 μg (e.g., 4.0 μg/mL in 60 ml or 6.0 μg/mL in 40 ml) and bevacizumab administered was 7.5 mg/kg with three weeks between administration of the MDNA55 and the bevacizumab. The volume of infusion was adjusted based on tumor size in each subject. MDNA55 and Avastin were administered separately and at least two weeks apart (e.g., 2, 3, 4, 5 or 6 weeks).

Infusion via each catheter was initiated at the rate of 3 μL/min/catheter and gradually increased in a stepwise manner. The infusion flow rate was adjusted at the discretion of the Investigator during real time MRI (with subject maintained under anesthesia) provided that the flow rate per catheter did not exceed 10 μL/min. The flow rate was established such that the duration of infusion was at least 24 hours to a maximum of approximately 48 hours. After the real-time MRI infusion monitoring period was completed, the remainder of the infusion continued with the subject awake. MRI was performed upon completion of infusion as a final evaluation of the infusate distribution.

Figure 2:
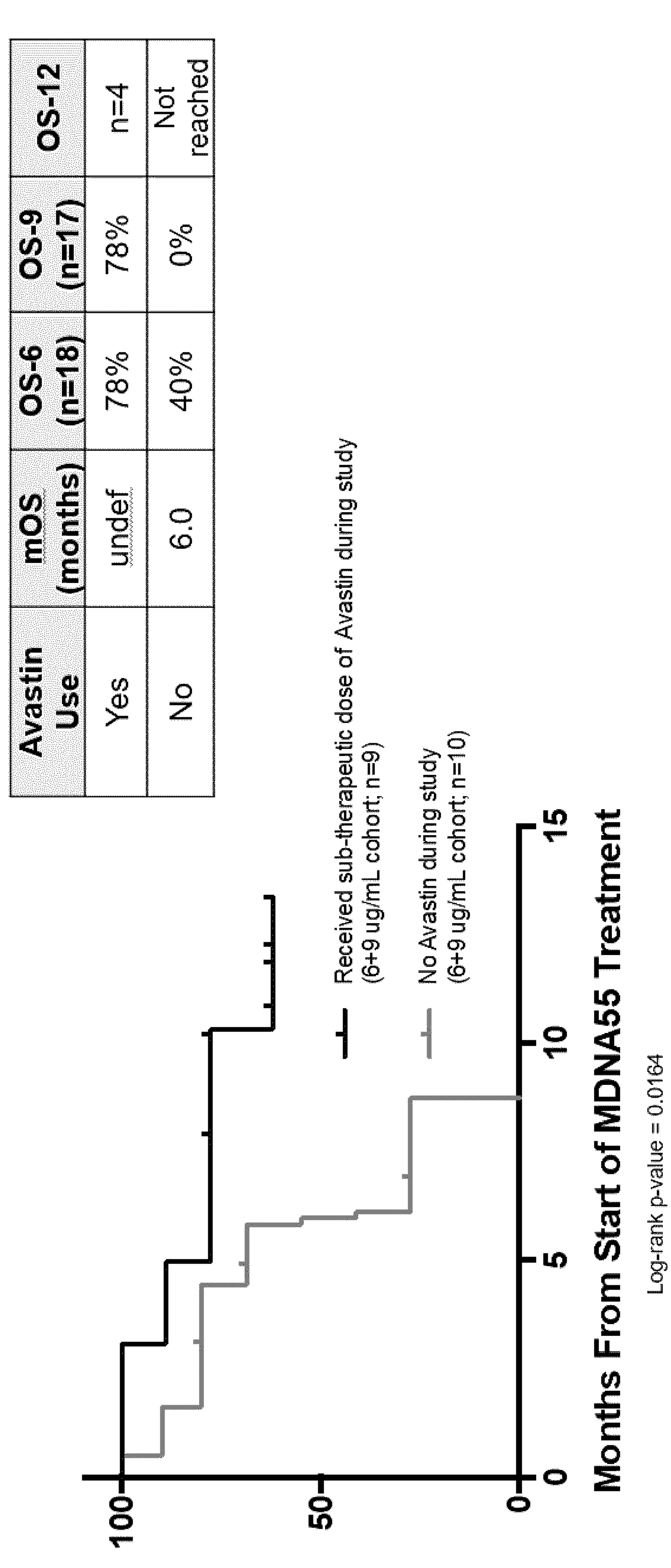
FIG. 2. Provides data regarding subjects receiving sub-therapeutic dose of Avastin following MDNA55 treatment showing longer survival. As provided in example 1, MDNA55 was administered to patients at 6.0 μg/mL or 9.0 μg/mL and the sub-therapeutic dose of Avastin administered was between 5 mg/kg every two weeks to 7.5 mg/kg every three weeks.
Figure 3:
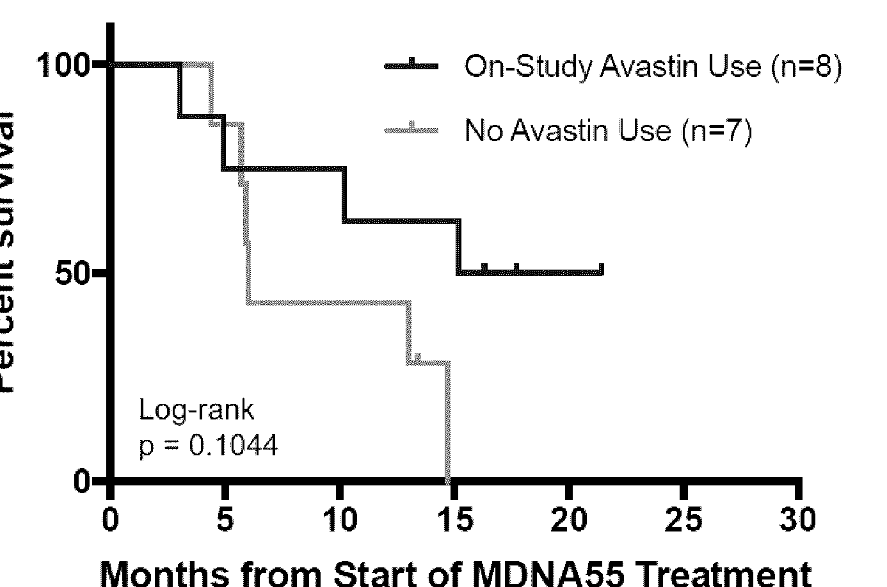
FIG. 3. Provides data regarding subjects receiving Sub-Therapeutic Dose of Avastin following MDNA55 treatment showing longer survival. As provided in example 1, MDNA55 was administered to patients at 6.0 μg/mL or 9.0 μg/mL and the sub-therapeutic dose of Avastin administered was between 5 mg/kg every two weeks to 7.5 mg/kg every three weeks.

After the above treatment with MDNA55 and bevacizumab or MDNA55 alone, survival of each subject was followed until death (or termination of data collection by the Sponsor or withdrawal of consent by the subject). As shown FIGS. 1-3, subjects treated with MDNA55 in combination with a subtherapeutic level of bevacizumab showed increased survival time from treatment until death (mOS) compared to the subjects treated with MDNA55 alone. The survival time achieved is advantageous over prior art treatments for glioblastoma.

Example II. Biomarker Analysis of IL4R Expression

Archived tumor tissue specimens from the above subjects was processed by IHC at a CLIA certified laboratory (QualTek Molecular Laboratories, Goleta, CA) for retrospective analysis of IL4R expression to determine if there is a correlation between IL4R expression and tumor response following the MDNA55 and bevacizumab combination treatment.

Tissue sections were graded for IL4R expression by examining staining intensity in a blinded fashion for each specimen using a semi-quantitative scale of 0, 1+, 2+, and 3+ (as well as HScore). Further quantitative assessment of IL4R staining may include standardized image analysis. Efficacy endpoints, such as progression-free survival (PFS), objective response rate (ORR), overall survival (OS), duration of response (DOR), and duration of clinical benefit (DOCB) were evaluated versus intensity of IL4R expression.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treating a central nervous system (CNS) tumor in a subject, comprising administering to the subject MDNA55 (SEQ ID NO: 1) in combination with a vascular endothelial growth factor A (VEGF-A) inhibitor administered at a subtherapeutic level,
   wherein the VEGF-A inhibitor is administered at least two weeks apart from the MDNA55;
   wherein the VEGF-A inhibitor is bevacizumab or a biosimilar of bevacizumab; and
   wherein the CNS tumor is an IL-4 receptor (IL-4R)-positive CNS tumor.

2. A method of inhibiting a central nervous system (CNS) tumor in a subject that is characterized by IL-4 receptor (IL-4R) expression, comprising:
   a) contacting the CNS tumor with MDNA55 (SEQ ID NO: 1); and
   b) contacting the CNS tumor with a subtherapeutic level of a vascular endothelial growth factor A (VEGF-A) inhibitor at least two weeks apart from the contact with the MDNA55,
   wherein the VEGF-A inhibitor is bevacizumab or a biosimilar of bevacizumab.

3. The method according to claim 1, wherein the CNS tumor is a recurrent CNS tumor or a newly diagnosed CNS tumor.

4. The method according to claim 3, wherein the CNS tumor is a recurrent or refractory glioblastoma.

5. The method according to claim 1, wherein the CNS tumor is selected from the group consisting of glioma, glioblastoma, astrocytoma, medulloblastoma, craniopharyngioma, ependymoma, pinealoma, hemangioblastoma, acoustic neuroma, oligodendroglia, meningioma, meningioma, neuroblastoma, and retinoblastoma.

6. The method according to claim 1, wherein the MDNA55 is administered as a single dose of about 90 μg, about 180 μg, or about 240 μg.

7. The method according to claim 6, wherein the MDNA55 is administered as a single dose of about 1.5 μg/mL in 60 mL, about 4.5 μg/mL in 40 mL or 3 μg/mL in 60 mL, or about 6 μg/mL in 40 mL or 4 μg/mL in 60 mL.

8. The method according to claim 1, wherein the MDNA55 is formulated in an artificial cerebral spinal fluid (CSF) solution and albumin.

9. The method according to claim 1, wherein the MDNA55 is administered intratumorally.

10. The method according to claim 9, wherein the intratumoral administration comprises intracranial administration.

11. The method according to claim 1, wherein the MDNA55 is administered via an intracranial catheter or by convection-enhanced delivery (CED), optionally wherein the MDNA55 is administered via one or more intracranial catheters.

12. The method according to claim 11, wherein the MDNA55 is administered through the catheter with a flow rate of about 5 μL/min/catheter to about 20 μL/min/catheter or a flow rate of about 15 μL/min/catheter.

13. The method according to claim 1, wherein the biosimilar of bevacizumab is selected from bevacizumab-awwb, bevacizumab-bvzr, Aybintio, MYL-14020, FKB238, BCD-021, BCD500, Krabeva, BAT1706, BI 695502, CT-P16, CHS-5217, DRZ_BZ, Lumiere, Cizumab, IBI-305, MIL60, Bevax, ONS-1045, HD204, Bevacirel, HLX04, and TX16.

14. The method according to claim 1, wherein the subtherapeutic dose of the VEGF-A inhibitor is below 10 mg/kg, or from 1 mg/kg to 7.5 mg/kg.

15. The method according to claim 1, wherein the VEGF-A inhibitor is administered after the MDNA55.

16. The method according to claim 1, wherein the VEGF-A inhibitor is administered before the MDNA55.

17. The method according to claim 1, wherein the VEGF-A inhibitor is administered at least two weeks apart from the MDNA55 for a period of at least 12 weeks, 16 weeks, 20 weeks, 24 weeks, 30 weeks, 36 weeks, 40 weeks, 44 weeks, 48 weeks, 52 weeks or more.

* * * * *

```
                         SEQUENCE LISTING

<160> NUMBER OF SEQ ID NOS: 1

<210> SEQ ID NO 1
<211> LENGTH: 485
<212> TYPE: PRT
<213> ORGANISM: Artificial Sequence
<220> FEATURE:
<223> OTHER INFORMATION: Synthetic

<400> SEQUENCE: 1

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Leu Arg Asp Arg Asn Leu Trp Gly Leu Ala Gly Leu Asn Ser Cys Pro
    50                  55                  60
```

```
Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Lys Ala Ser Gly Gly Pro Glu Gly Gly Ser
    130                 135                 140

Leu Ala Ala Leu Thr Ala His Gln Ala Cys His Leu Pro Leu Glu Thr
145                 150                 155                 160

Phe Thr Arg His Arg Gln Pro Arg Gly Trp Glu Gln Leu Glu Gln Cys
                165                 170                 175

Gly Tyr Pro Val Gln Arg Leu Val Ala Leu Tyr Leu Ala Ala Arg Leu
            180                 185                 190

Ser Trp Asn Gln Val Asp Gln Val Ile Arg Asn Ala Leu Ala Ser Pro
        195                 200                 205

Gly Ser Gly Gly Asp Leu Gly Glu Ala Ile Arg Glu Gln Pro Glu Gln
    210                 215                 220

Ala Arg Leu Ala Leu Thr Leu Ala Ala Ala Glu Ser Glu Arg Phe Val
225                 230                 235                 240

Arg Gln Gly Thr Gly Asn Asp Glu Ala Gly Ala Ala Asn Gly Pro Ala
                245                 250                 255

Asp Ser Gly Asp Ala Leu Leu Glu Arg Asn Tyr Pro Thr Gly Ala Glu
            260                 265                 270

Phe Leu Gly Asp Gly Gly Asp Val Ser Phe Ser Thr Arg Gly Thr Gln
        275                 280                 285

Asn Trp Thr Val Glu Arg Leu Leu Gln Ala His Arg Gln Leu Glu Glu
    290                 295                 300

Arg Gly Tyr Val Phe Val Gly Tyr His Gly Thr Phe Leu Glu Ala Ala
305                 310                 315                 320

Gln Ser Ile Val Phe Gly Gly Val Arg Ala Arg Ser Gln Asp Leu Asp
                325                 330                 335

Ala Ile Trp Arg Gly Phe Tyr Ile Ala Gly Asp Pro Ala Leu Ala Tyr
            340                 345                 350

Gly Tyr Ala Gln Asp Gln Glu Pro Asp Ala Arg Gly Arg Ile Arg Asn
        355                 360                 365

Gly Ala Leu Leu Arg Val Tyr Val Pro Arg Ser Ser Leu Pro Gly Phe
    370                 375                 380

Tyr Arg Thr Ser Leu Thr Leu Ala Ala Pro Glu Ala Ala Gly Glu Val
385                 390                 395                 400

Glu Arg Leu Ile Gly His Pro Leu Pro Leu Arg Leu Asp Ala Ile Thr
                405                 410                 415

Gly Pro Glu Glu Glu Gly Gly Arg Leu Glu Thr Ile Leu Gly Trp Pro
            420                 425                 430

Leu Ala Glu Arg Thr Val Val Ile Pro Ser Ala Ile Pro Thr Asp Pro
        435                 440                 445

Arg Asn Val Gly Gly Asp Leu Asp Pro Ser Ser Ile Pro Asp Lys Glu
    450                 455                 460
```

-continued

```
Gln Ala Ile Ser Ala Leu Pro Asp Tyr Ala Ser Gln Pro Gly Lys Pro
465                 470                 475                 480

Pro Lys Asp Glu Leu
                485
```